(12) United States Patent
Zhukov et al.

(10) Patent No.: US 8,923,598 B2
(45) Date of Patent: Dec. 30, 2014

(54) METHODS AND APPARATUS FOR DIAGNOSIS AND/OR PROGNOSIS OF CANCER

(71) Applicant: H. Lee Moffitt Cancer Center and Research Institute, Inc., Tampa, FL (US)

(72) Inventors: Tatyana A. Zhukov, Lutz, FL (US); Dansheng Song, Tampa, FL (US); Melvyn S. Tockman, Tampa, FL (US)

(73) Assignee: H. Lee Moffitt Cancer Center and Research Institute, Tampa, FL (US)

( * ) Notice: Subject to any disclaimer, the term of this patent is extended or adjusted under 35 U.S.C. 154(b) by 0 days.

(21) Appl. No.: 14/212,812

(22) Filed: Mar. 14, 2014

(65) Prior Publication Data

US 2014/0193062 A1  Jul. 10, 2014

Related U.S. Application Data

(63) Continuation of application No. 13/383,801, filed as application No. PCT/US2010/001955 on Jul. 13, 2010, now Pat. No. 8,737,715.

(60) Provisional application No. 61/225,003, filed on Jul. 13, 2009.

(51) Int. Cl.
| | |
|---|---|
| *G06K 9/00* | (2006.01) |
| *G01N 33/50* | (2006.01) |
| *G01N 33/574* | (2006.01) |
| *G06T 7/00* | (2006.01) |
| *C12Q 1/68* | (2006.01) |
| *G01N 33/48* | (2006.01) |
| *A61B 10/02* | (2006.01) |

(52) U.S. Cl.
CPC .......... *G06K 9/0014* (2013.01); *G01N 33/5076* (2013.01); *G01N 33/574* (2013.01); *G06T 7/0012* (2013.01); *A61B 10/02* (2013.01); *G01N 2800/52* (2013.01)
USPC ............................ 382/133; 435/6.14; 436/64

(58) Field of Classification Search
CPC ............... G06K 9/00; G01N 1/00; A61B 1/00
USPC ......... 382/128, 129, 130, 131, 132, 133, 134, 382/164, 190; 600/300, 407, 410, 411, 425, 600/427; 435/6.14, 7.23, 330, 344; 436/64, 436/813
See application file for complete search history.

(56) References Cited

U.S. PATENT DOCUMENTS 8,029,784 B2 * 10/2011 Bates et al. ................. 424/130.1
8,227,202 B2 * 7/2012 Fantl et al. .................. 435/7.21
(Continued)

OTHER PUBLICATIONS

Berrut, J.P. et al. "Barycentric Lagrange Interpolation" *Siam Review*, 2004, 46(3):501-517.

(Continued)

*Primary Examiner* — Abolfazl Tabatabai
(74) *Attorney, Agent, or Firm* — Saliwanchik, Lloyd & Eisenschenk

(57) ABSTRACT

The subject invention concerns methods for the detection, diagnosis, and/or prognosis of cancer by analyzing centrosomal features. In one embodiment, a method includes receiving an image of one or more cells; selecting a region of interest in one cell; segmenting the region of interest to delineate at least one centrosomal; extracting one or more features from the segmented image; and analyzing the extracted features to diagnose cancer. In another embodiment, the progression of cancer can be predicted through analysis and classification of the extracted features. In one embodiment, the method can be performed by a quantitative cancer analysis system including a diagnosis module and/or a prognosis module. In one embodiment, the method can be performed using an image processing system.

20 Claims, 24 Drawing Sheets
(5 of 24 Drawing Sheet(s) Filed in Color)

(56) References Cited

U.S. PATENT DOCUMENTS 8,737,715 B2 * 5/2014 Zhukov et al. ............ 382/133
2004/0115697 A1 6/2004 Doxsey et al.

OTHER PUBLICATIONS

Guo, H.Q. et al. "Analysis of the cellular centrosome in fine-needle aspirations of the breast" *Breast Cancer Research*, 2007, 9(4):R48 (7 pages).

Hsu, L.C. et al. "Centrosome abnormalities in ovarian cancer" *Int. J. Cancer*, 2005, 113:746-751.

Kawamura, K. et al. "Centrosome Hyperamplification and Chromosomal Instability in Bladder Cancer" *European Urology*, 2003, 43:505-515.

Landen, C.N. et al. "Overexpression of the Centrosomal Protein Aurora—A Kinase is Associated with Poor Prognosis in Epithelial Ovarian Cancer Patients" *Clin Cancer Res*, Jul. 15, 2007, 13(14):4098-4104.

Lehmann, F. et al. "Clinical response to the MAGE—A3 immunotherapeutic in metastatic melanoma patients is associated with a specific gene profile present prior to treatment" *Cancer Immunity*, Dec. 15, 2008, 8(2):27, abstract.

Lentini, L. et al. "Simultaneous Aurora-A/STK15 overexpression and centrosome amplification induce chromosomal instability in tumour cells with a MIN phenotype" *BMC Cancer*, Nov. 13, 2007, 7:212 (13 pages).

Michalak, K. et al. "Correlation-Based Feature Selection Strategy in Classification Problems" *Int. J. Appl. Math. Comput. Sci.*, 2006, 16(4):503-511.

Pihan, G.A. et al. "Centrosome Defects Can Account for Cellular and Genetic Changes That Characterize Prostate Cancer Progression" *Cancer Res*, Mar. 1, 2001, 61:2212-2219.

Saunders, W. "Centrosomal amplification and spindle multipolarity in cancer cells" *Seminars in Cancer Biology*, 2005, 15:25-32.

Shinmura, K. et al. "Induction of centrosome amplification and chromosome instability in *p*53-deficient lung cancer cells exposed to benzo[a]pyrene diol epoxide )B[a]PDE)" *J Pathol*, 2008, 216:365-374.

Shono, M. et al. "Stepwise Progression of Centrosome Defects Associated with Local Tumor Growth and Metastatic Process of Human Pancreatic Carcinoma Cells Transplated Orthotopically inton Nude Mice" *Laboratory Investigation*, Jul. 2001, 81(7):945-952.

Terriberry, T.B. etal. "Hypothesis Testing with Nonlinear Shape Models" *Information Processing in Medical Imaging*, 2005, 3565:15-26.

Yin, P.Y. et al. "Maximum entropy-based optimal threshold selection using deterministic reinforcement learning with controlled randomization" *Signal Processing*, 2002, 82:993-1006.

\* cited by examiner

METHODS AND APPARATUS FOR DIAGNOSIS AND/OR PROGNOSIS OF CANCER

CROSS-REFERENCE TO RELATED APPLICATIONS

The present application is a continuation of U.S. application Ser. No. 13/383,801, filed Mar. 20, 2012, which is the National Stage of International Application Number PCT/US2010/001955, filed Jul. 13, 2010, which claims the benefit of U.S. Provisional Application Ser. No. 61/225,003, filed Jul. 13, 2009, each of which is hereby incorporated by reference herein in its entirety, including any figures, tables, or drawings.

FIELD OF INVENTION

This invention relates to the detection, diagnosis, and/or prognosis of cancers. Specifically, the invention provides an imaging algorithm to analyze centrosomal features in order to distinguish cancer cells from normal cells and prognose long term from short term survival cancer patients.

BACKGROUND OF INVENTION

The centrosome is a cellular organelle that functions as the microtubule organizing center of interphase and mitotic cells (Nigg (2002)). The centrosome duplicates itself only once during each cell cycle with duplication beginning near the G1-S transition and completing during the G2 phase. Duplicated centrosomes separate to produce two mitotic spindle poles that organize the mitotic apparatus. Centrosomes play critical roles in processes that ensure proper segregation of chromosomes and maintain the genetic stability of human cells (Shinmura et al. (2008); Fukasawa (2007)). Centrosomal defects were originally proposed to lead to aneuploidy and cancer in 1914 by Boveri (Wunderlich (2002); Brinkley et al. (1998)). He saw that cancer cells commonly have centrosomal defects including increased centrosome number and postulated that changes in centrosome functionality may be key to cancer formation. Centrosomal abnormalities are detected in various types of human cancers, e.g., cancers of the lung, breast, gall bladder, bone, pancreas, colorectal, head, neck, prostate and ovaries (Bourke et al. (2007); Saunders (2005)) and rarely observed in normal tissue (Saunders (2005)). It is believed that cancer cells commonly have centrosomal defects. Most researches have found that centrosomal defects occurred at a very early premalignant stage of tumor formation, prior to the appearance of detectable lesions. Centrosomal defects have been found to increase in severity during tumor progression. Recent evidence indicates that loss of centrosomal integrity may be a major cause of chromosomal instability underlying various human cancers (Fukasawa (2007); Bourke et al. (2007); Lentini et al. (2007); Landen et al. (2007)). Aneuploidy of nonsmall cell lung cancer is associated with centrosomal abnormalities (Jung et al. (2007)). In the lung, important findings suggest that centrosomal abnormalities may develop at a relatively early stage of lung carcinogenesis. Moreover, it was shown that stepwise progression of centrosome defects is associated with local lung tumor progression to a more advanced stage, and with accelerating the metastatic process of lung carcinoma cells (Koutsami et al. (2006)).

Lung cancer is the most common cause of cancer mortality for both men and women. In 2009, the American Cancer Society estimated the numbers of lung cancer cases were 219,440 and lung cancer resulted in 159,390 deaths in the United States (Jemal et al. (2009)). In contrast, colorectal, breast, and prostate cancers combined were 117,890 deaths. Once diagnosed, prognosis and treatment depend upon lung cancer staging, which considers tumor size and extent, nodal involvement and distant metastasis (AJCC, (1998)). The five-year survival rates by clinical stages were IA 50%, IB 47%, IIA 36%, IIB 26%, IIIA 19%, IIIB 7%, and IV 2% (Rami-Porta et al. (2009)). Cancer detected in early stages have higher survival rate. Unfortunately, the prognosis of stage I lung cancer is highly variable. Post operative recurrence of stage I non-small cell lung carcinoma (NSCLC) leads to early mortality in approximately 40%, with current pathology indices unable to distinguish those with poor prognosis (Woo, (2009)). In our preliminary data (35 cases), there are four cases who have survived nine years or more (still alive) and three deceased cases who survived four years or less (four, three, and two years, respectively) in stage IA; there are two cases who've survived nine years or more (remain alive) and six deceased cases who survived four years or less (one case survived less than one year, two cases survived one year, three cases survived four, three, two years, respectively) in stage IB. In our study of patients with stage I lung cancer, clinical techniques could not distinguish stage I patients into long term survivors and short term survival (fatality) groups. Molecular prognostic and diagnostic cancer markers should have a high prevalence, and the techniques to measure these markers must have high sensitivity and specificity. Examination of tumor cell organelles or markers can provide a method to accurately diagnose and recognize the prognosis of individual stage I NSCLC to enable timely and personalized administration of therapy (Kwiatkowski et al. (1998); D'Amico et al. (2000); D'Amico (2002)).

BRIEF SUMMARY OF THE INVENTION

The subject invention concerns methods and apparatus for the detection, diagnosis, and/or prognosis of cancer in a person or animal by analyzing centrosomal features. In one embodiment, a method of the invention includes receiving an image of one or more cells; selecting a region of interest in one cell; segmenting the region of interest in the one cell to delineate or isolate at least one centrosome; extracting one or more features from the segmented image; and analyzing the extracted features to diagnose cancer. In another embodiment, the progression of cancer can be predicted through analysis of the extracted features. In one embodiment, methods of the invention can be performed by a quantitative cancer analysis system including a diagnosis module and/or a prognosis module. In one embodiment, the method can be performed using an image processing system. Methods of the invention can be used to distinguish longer term cancer survival patients from shorter term cancer survival patients.

In one embodiment, a total of 11 centrosomal features are extracted, calculated, and analyzed using, for example, image processing and feature analysis. The centrosomal features which can be utilized in the methods include counting centrosomal number per cell; calculating centrosomal size; checking centrosomal fragment; measuring centrosomal intensity and its standard deviation (2 features); and describing centrosomal shape from different aspects (6 features). High resolution images of cells are acquired and then followed up with one or more of image pre-processing (e.g., image enhancement), segmentation, feature extraction, and statistical analysis. In one embodiment, the statistical analysis includes two-sample t-test and/or two-sample Kolmogorov-Smirnov (K-S) test. The features discussed herein are illustrative. Other features can be extracted and analyzed.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A and 1B are original images under 100× oil-immersion objective, for a total magnification of 1000×. FIGS. 1C and 1D are two full color centrosome region of interest (ROI) images taken from FIGS. 1A and 1B, respectively. FIGS. 1E and 1F are histograms of FIGS. 1C and 1D. FIGS. 1G and 1H are the red channel histograms of FIGS. 1C and 1D. t in FIGS. 1G and 1H are optimized thresholds.

FIG. 2A shows a color RGB image of region of interest (ROI) taken from untreated cancer cell image, which includes centrosomes belonging to this cell. FIG. 2B shows an interpolated image of FIG. 2A, its size is twice that of the image in FIG. 2A. To balance the image processing time and resolution of image, two times interpolation is chosen.

FIG. 3A: interpolated image. FIG. 3B: the red channel of RGB FIG. 3A. This channel shows the signal from the 594 laser reading the Alexa Fluor 594 secondary antibody bound to γ-Tubulin, all centrosome information can be found in this channel. FIG. 3C: the segmented image of FIG. 3B. This binary image will be used as the mask for separating centrosomes from the background. FIG. 3D: centrosomes are isolated from other parts of the image. It is analyzed in the red channel. It is ready for feature extraction.

FIG. 6A is a tissue image, stained with γ-Tubulin antibody; in which centrosomes are shown as red spots. FIGS. 6B and 6C are two Regions of Interest (ROI). Images selected from FIGS. 6A, 6D, and 6E are segmentation images of FIGS. 6B and 6C, from which centrosomes are isolated from background and ready for feature extraction.

DETAILED DESCRIPTION OF THE INVENTION

Figure 1A:
FIGS. 1A-1H.

The subject invention concerns methods and apparatus for the detection, diagnosis, and/or prognosis of cancer in a person or animal by analyzing centrosomal features. In one embodiment, the method includes receiving an image of one or more cells; selecting a region of interest in one cell; segmenting the region of interest in the one cell to delineate or isolate at least one centrosome; extracting one or more centrosomal features from the segmented image; and analyzing the extracted features to detect, diagnose, or provide a prognosis of cancer. Optionally, the results of the analysis can be subjected to a classifying process, e.g., to classify whether a result falls into a cancer or normal category or a long-term survivor or a short-term survivor category. In another embodiment, the progression of cancer can be predicted through analysis of the extracted features. In one embodiment, the method further comprises obtaining a sample of tissue or cells from the person or animal. Cancer cells and tissues for analysis also may be obtained from biopsy (including bronchial brushing or washing) or resected cancer specimens, or from biological fluid samples (e.g., blood, saliva, lymph, etc.). Cancer cells may be formalin fixed and paraffin embedded or preserved in OCT by flash freezing. Circulating tumor cells also may be obtained for analysis from samples of blood, sputum, or urine, immobilized on a slide or in the channels of a microfluidic device. In one embodiment, the method can be performed by a quantitative cancer analysis system including a diagnosis module and/or a prognosis module. In one embodiment, the method can be performed using an image processing system.

In one embodiment of the present invention, centrosomal features are quantitatively measured. Herein, several centrosomal features are discussed, which can be extracted, calculated, and analyzed using image processing, for example. In one embodiment, one centrosomal feature is counting centrosomal number per cell, one feature is calculation of centrosomal size, one feature is checking centrosomal fragment, two features are measures of centrosomal intensity and its standard deviation, and six features are descriptions of centrosomal shape from different aspects. Other features that can be utilized in the subject invention include texture features, such as Angular second moment, Contrast, Correlation, Sum of squares: Variance, Inverse difference moment, Sum average, Sum variance, Sum entropy, Entropy, Difference variance, Difference entropy, Information measures of correlation, and Maximal correlation coefficient. Additional features that can be used in the subject invention include consistency/ heterogeneity of individual centrosomal features (e.g., number, area, fragment, etc.). In one embodiment, at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five centrosomal feature(s) is (are) extracted and analyzed. Centrosomal features that can be utilized in the present invention include, but are not limited to, centrosomal number/cell, area, fragment, intensity, intensity standard deviation, area/box, aspect, mean diameter, perimeter ratio, roundness, fractal dimension, solidity, eccentricity, and some texture features. In a specific embodiment, six centrosomal features are extracted and analyzed. In an exemplified embodiment, the features extracted and analyzed comprise number/cell, area, roundness, intensity, perimeter ratio, and fractal dimension. In another specific embodiment, five centrosomal features are extracted and analyzed. In an exemplified embodiment, the features extracted and analyzed comprise centrosome number/cell, area, intensity, fragment, and aspect.

Results that support detection or diagnosis of cancer include, but are not limited to, where centrosomal number/cell is increased compared to the number/cell of normal cells; centrosomal area is deviated from the area of normal cells; centrosomal intensity is deviated from the intensity of normal cells; there is centrosomal fragment compared to no fragment of normal cells; centrosomal aspect is deviated from the aspect of normal cells. In one embodiment, the results obtained with the patient samples are compared to reference values of the extracted features for normal cells. The results are preferably statistically significant.

In one embodiment, high resolution images of tissue or cells can be acquired; then followed up with one or more of image pre-processing (e.g., image enhancement), image segmentation, feature extraction, and statistical analysis. In an embodiment, the statistical analysis implemented can be two-sample t-test and/or two-sample Kolmogorov-Smirnov test and/or Wilcoxon rank sum test. The features discussed herein are illustrative. Other features or combinations of features can be extracted and analyzed according to embodiments of the subject invention.

In one embodiment of the invention, the results of the analysis of the extracted features are subject to classification. If cancer is diagnosed using the subject method, then prognosis of the person or animal can be predicted following classifying the results of feature analysis into various categories (e.g., survival vs. fatality). In a specific embodiment, results are classified into a long-term survival or short-term survival category. In a specific embodiment, the extracted features that are analyzed comprise centrosomal number/cell, area, roundness, intensity, perimeter ratio, and fractal dimension. In an exemplified embodiment, the results are classified based on majority criterion, wherein if a majority of the analyzed centrosomes of a patient are classified into a long-term survival category, the patient will be given a prognosis for long-term survival, or if a majority of the analyzed centrosomes of a patient are classified into a short-term survival category, the patient will be given a prognosis for short-term survival. Results that support a prognosis of long-term survival of cancer, in one embodiment, include where centrosomal number/cell is increased compared to the number/cell from samples from short-term survivors; centrosomal area is decreased compared to the area from samples from short-term survivors; centrosomal roundness is decreased compared to the roundness from samples from short-term survivors; centrosomal intensity is increased compared to the intensity from samples from short-term survivors; centrosomal perimeter ratio is increased compared to the perimeter ratio from samples from short-term survivors; centrosomal fractal dimension is decreased compared to fractal dimension from samples from short-term survivors. In one embodiment, the results obtained with the patient samples are compared to reference values of the extracted features for cells of long-term survivors and/or cells of short-term survivors. The results are preferably statistically significant.

In an embodiment, cancer is detected or diagnosed in an early stage. In another embodiment, a method of the invention provides a prognosis concerning treatment and/or survival of a cancer for a person or animal. Lung cancer is discussed herein as an illustrative example. The invention can be applied to other cancers including, for example, prostate cancer.

The subject invention can also be used to monitor and predict a patient's response to a cancer therapy (e.g., chemotherapy). Cells or tissue samples of a patients' cancer or tumor can be obtained and treated with an anti cancer therapeutic agent and the centrosomes of the cells monitored for reversal of one or more defects observed in centrosomal amplification of cancerous cells. In one embodiment, cancer cells can be analyzed using the methods of the subject invention to determine if treatment with a particular therapeutic agent (e.g., MLN8054, an Aurora kinase inhibitor, see Huck et al. (2010); Manfredi et al. (2007)) reverses or ameliorates mitotic spindle and segregation defects and chromosomal instability that are typically observed in centrosome amplification of cancer and tumor cells. If the particular treatment appears to have activity in reversing or ameliorating centrosomal defects of the cancer or tumor cells, then the clinician can predict that the tested treatment would be useful in treating the patient and the patient can be administered the particular treatment in a manner deemed most clinically appropriate. Similarly, if a particular treatment does not appear to have activity in reversing or ameliorating centrosomal defects of the cancer or tumor cells, then the clinician might predict that the tested treatment would not be useful in treating the patient and may decide not to administer the particular treatment to the patient and may determine that an alternate or modified treatment would be more likely to have a clinically beneficial effect for the patient. The subject invention can also be used to assess the response to a therapeutic treatment by evaluating centrosome amplification using the subject invention to assess the chromosomal instability associated with karyotypic convergence (Fukasawa (2008)). Changes in centrosomal features can also be monitored during cancer or tumor treatment to assist in determining whether the particular treatment regimen or protocol being administered to a patient is having a beneficial effect on destruction, reduction, or inhibition of the cancer or tumor. For example, if during treatment, there is minimal or no reversal or amelioration of defects associated with centrosomal amplification, then the patient's treatment might be modified or changed in a clinically appropriate manner.

Figure 11:
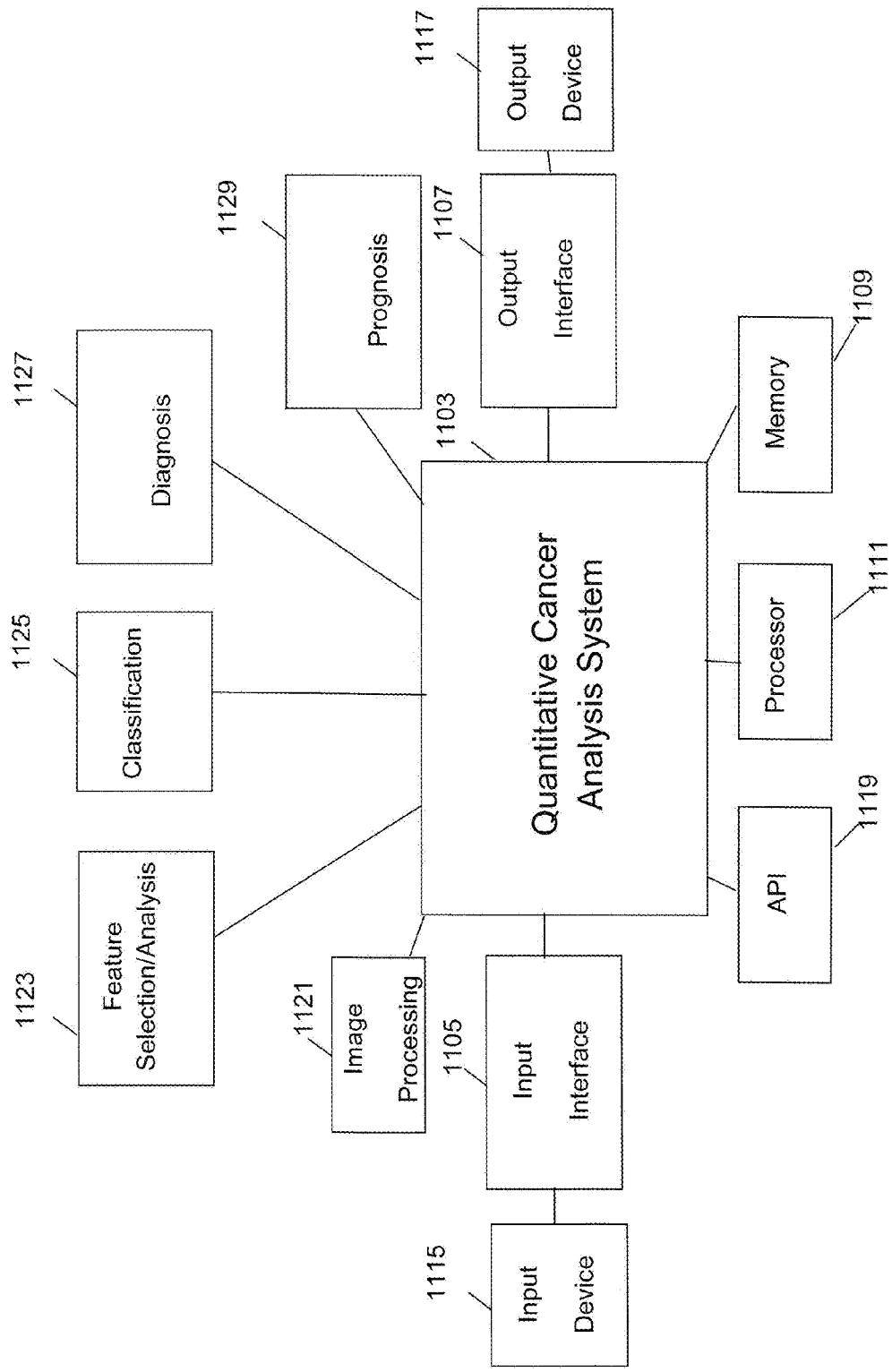
FIG. 11 is a functional block diagram a quantitative cancer analysis system in accordance with an embodiment of the subject invention.

FIG. 11 is a functional block diagram of a quantitative cancer analysis system 1103 in accordance with an embodiment of the subject invention. The system 1103 is only an illustrative embodiment of the invention. Other embodiments of such a system may include more, fewer, or different components. Or the components shown may be differently arranged.

In the embodiment shown, the quantitative cancer analysis system 1103 includes an input interface 1105, an output interface 1107, memory 1109 for program storage and/or data storage, and a processor 1111 for processing information. In an embodiment, the input interface 1105 includes an input device 1115 such as a mouse or other pointing device, a keyboard, or a communication device such a modem or other network interface. In a particular embodiment, the input device 1115 is an imaging device such as a microscope. In another embodiment, the quantitative cancer analysis system 1103 is incorporated into an image processing system such as the image processing system 1203 described below. Other input devices for receiving information are known in the art and can be used with the subject invention. In an embodiment, the input interface 1105 serves to translate data received from the input device 1115 into a format usable by the quantitative cancer analysis system 1103. Thus, the input device 1115 and the input interface 1105 can be replaced without modifying the quantitative cancer analysis system 1103 as known in the art. In an embodiment, the output interface 1107 includes an output device 1117 such as a monitor, printer, projector, or other display device, a speaker or other audio device, or a communication device such as a modem. Other output devices for presenting information are known in the art and can be used with the subject invention. In an embodiment, the output interface 1107 serves to translate data received from the quantitative cancer analysis system 1103 into a format usable by the output device 1117. Thus, the output device 1117 and the output interface 1107 can be replaced without modifying the quantitative cancer analysis system 1103 as known in the art. In an embodiment, the quantitative cancer analysis system 1103 includes an application interface 1119 for sharing information with other applications. For example, the quantitative cancer analysis system 1103 can include an interface for communicating with an electronic medical records system. In an embodiment, the memory 1109 includes computer-readable media embodying a computer-program product as described above. In an embodiment, the memory includes a database or other device for data storage. Other memory devices are known in the art and can be used with the subject invention. In an embodiment, the quantitative cancer analysis system 1103 includes multiple input interfaces 1105, output interfaces 1107, memories 1109, processors 1111, input devices 1115, output devices 1117, or APIs 1119.

In an embodiment, the quantitative cancer analysis system 1103 includes one or more program modules, such as a image processing module 1121, a feature selection/analysis module 1123, a classification module 1125, a diagnosis module 1127, and/or a prognosis module 1129, as further described below.

Figure 12:
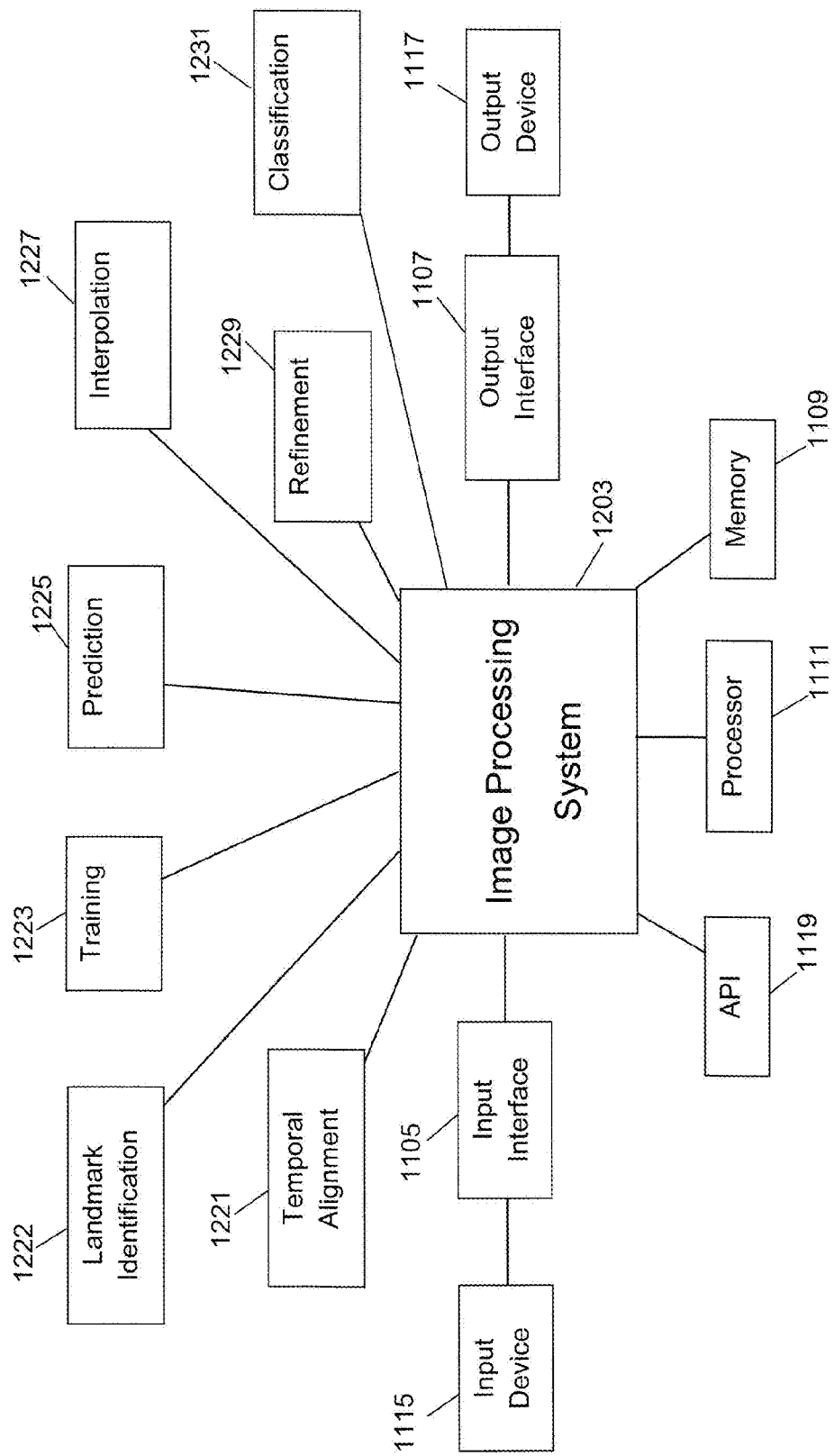
FIG. 12 is a functional block diagram an image processing system in accordance with an embodiment of the subject invention.

FIG. 12 is a functional block diagram of an image processing system 1203 in accordance with an embodiment of the subject invention. The system 1203 is only an illustrative embodiment of the invention. Other embodiments of such a system may include more, fewer, or different components. Or the components shown may be differently arranged.

In the embodiment shown, the image processing system 1203 includes one or more of an input interface 1105, output interface 1107, memory 1109, processor 1111, input device 1115, output device 1117, and/or application interface 1119 as described above.

In an embodiment, the image sequence processing system 1203 includes one or more program modules, such as a temporal alignment module 1221, a landmark identification module 1222, a training module 1223, a prediction module 1225, an interpolation module 1227, a refinement module 1229, and/or a classification module 1231, as further described below.

Figure 13:
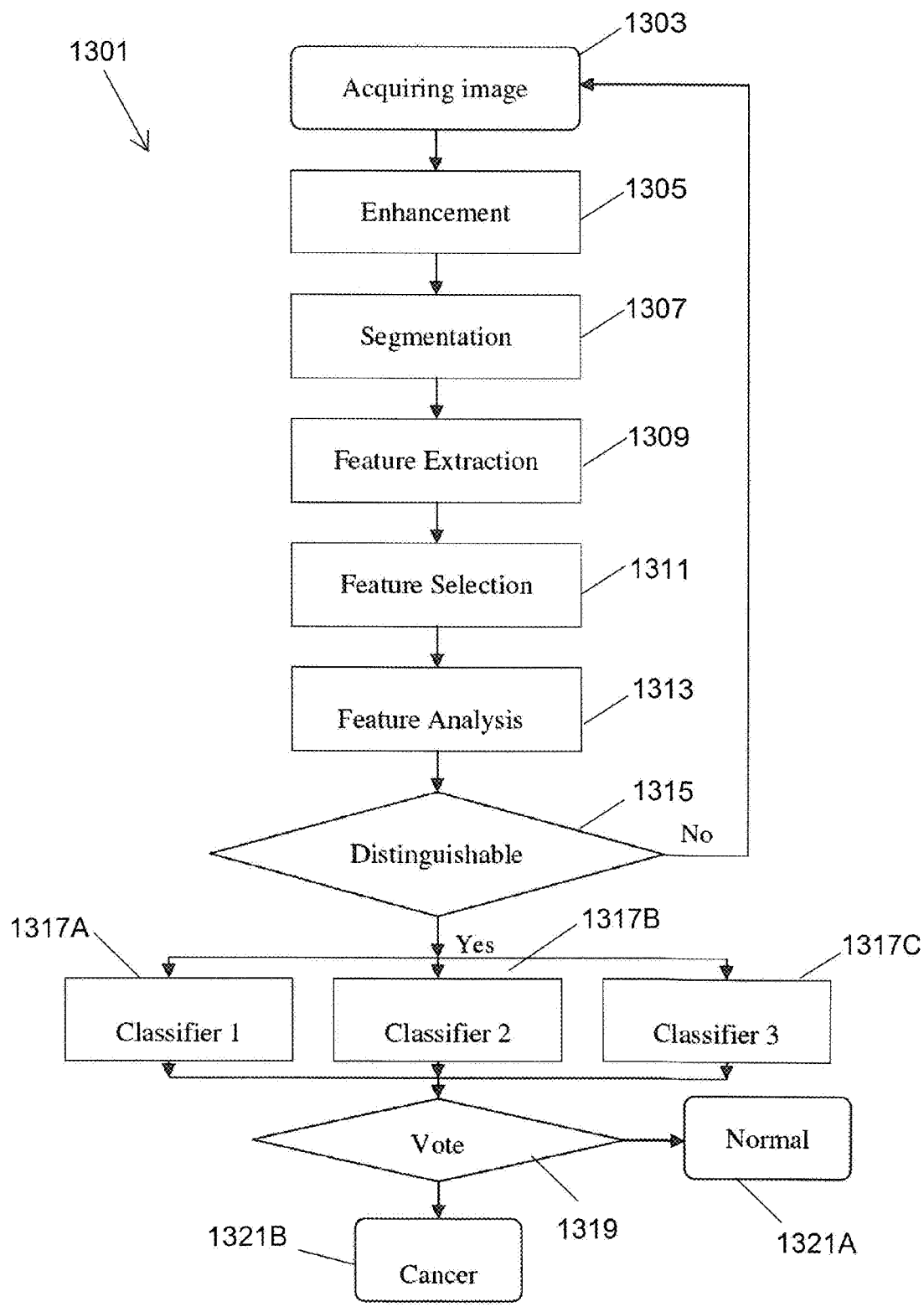
FIG. 13 is a flowchart of a method for diagnosing cancer in accordance with an embodiment of the subject invention.

FIG. 13 is a flowchart of a method 1301 for diagnosing cancer in accordance with an embodiment of the subject invention. The method 1301 is only an illustrative embodiment of the invention. Other embodiments of such a method may include more, fewer, or different steps. Or the steps shown may be differently arranged.

Figure 14:
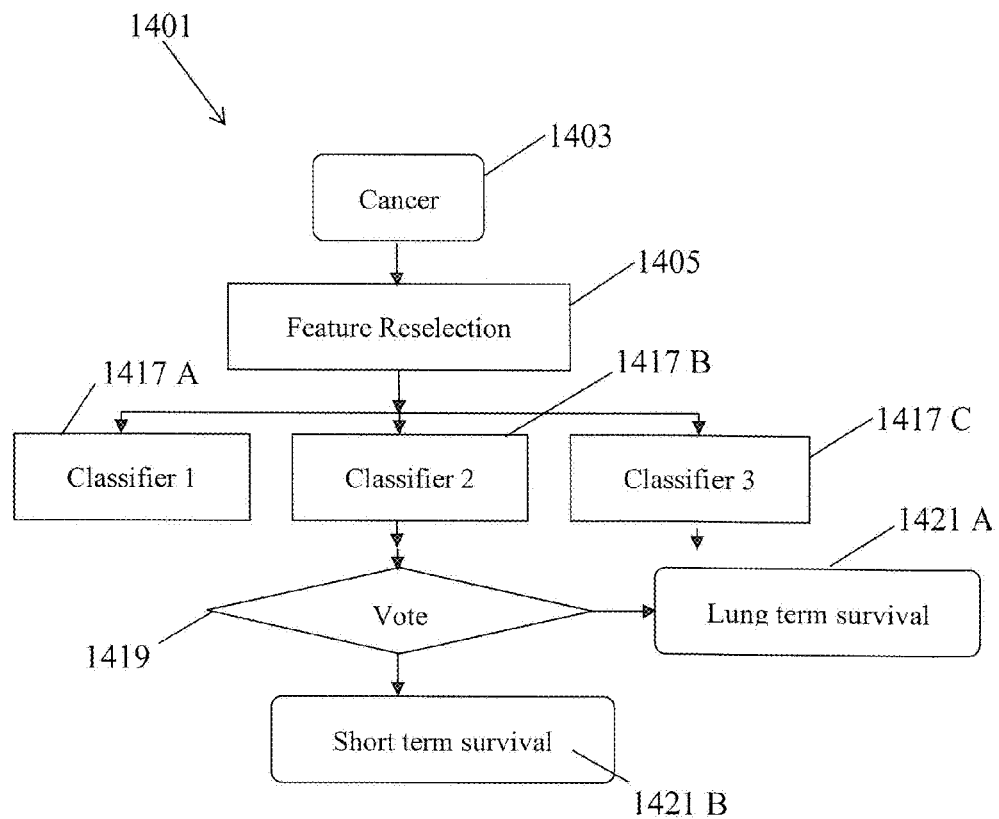
FIG. 14 is a flowchart of a method for prognosis of cancer in accordance with an embodiment of the subject invention.

FIG. 14 is a flowchart of a method 1401 for prognosis of cancer in accordance with an embodiment of the subject invention. The method 1401 is only an illustrative embodiment of the invention. Other embodiments of such a method may include more, fewer, or different steps. Or the steps shown may be differently arranged.

In an embodiment, one or more of steps of a method for diagnosing cancer are performed by one or more suitably programmed computers. In a particular embodiment, at least one of the method steps is performed by the one or more suitably programmed computers. Computer-executable instructions for performing these steps can be embodied on one or more computer-readable media as described below. In an embodiment, the one or more suitably programmed computers incorporate a processing system as described below. In an embodiment, the processing system is part of a quantitative cancer analysis system and/or image processing system.

In an embodiment, one or more of steps of a method for prognosis of cancer are performed by one or more suitably programmed computers. In a particular embodiment, at least one of the method steps is performed by the one or more suitably programmed computers. Computer-executable instructions for performing these steps can be embodied on one or more computer-readable media as described below. In an embodiment, the one or more suitably programmed computers incorporate a processing system as described below. In an embodiment, the processing system is part of a quantitative cancer analysis system and/or image processing system.

In an embodiment, computer-executable instructions for providing an interface can be embodied on one or more computer-readable media as described below. In an embodiment, the interface can be presented on one or more suitably programmed computers. In an embodiment, the one or more suitably programmed computers incorporate a processing system as described below. In an embodiment, the processing system is part of a quantitative cancer analysis system and/or image processing system.

In an embodiment, one or more components of a data structure are embodied on one or more computer-readable media as described below. In an embodiment, the data structure can be accessed via one or more suitably programmed computers. In an embodiment, the one or more suitably programmed computers incorporate a processing system as described below. In an embodiment, the processing system is part of a quantitative cancer analysis system and/or image processing system.

Aspects of the invention can be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, formats, and numerous other details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention can be practiced without these specific details. Computer systems, servers, work stations, and other machines can be connected to one another across a communication medium including, for example, a network or networks.

As one skilled in the art will appreciate, embodiments of the present invention can be embodied as, among other things: a method, system, or computer-program product. Accordingly, the embodiments can take the form of a hardware embodiment, a software embodiment, or an embodiment combining software and hardware. In an embodiment, the present invention takes the form of a computer-program product that includes computer-useable instructions embodied on one or more computer-readable media. Methods, data structures, interfaces, and other aspects of the invention described above can be embodied in such a computer-program product.

Computer-readable media include both volatile and nonvolatile media, removable and nonremovable media, and contemplate media readable by a database, a switch, and various other network devices. By way of example, and not limitation, computer-readable media incorporate media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments or modules to initiate a variety of tasks in response to data received in conjunction with the source of the received data.

The present invention can be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop, laptop, or tablet computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touchpad, touch-screen, or other pointing device, a keyboard, a camera, a monitor, a microphone, a speaker, a printer, a scanner, among other such devices. As further discussed above, the client devices can support various styles and types of client applications.

In one embodiment of a method of the invention, once detection, diagnosis, and/or prognosis is determined using the present invention, then treatment appropriate for the cancer diagnosed or prognosed in the patient can be implemented. Treatment can include, for example, surgery, chemotherapy, radiotherapy, etc. An ordinarily skilled clinician can determine an appropriate treatment regimen for a person or animal based on the diagnosis or prognosis provided by the subject invention for the particular cancer.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

Examples of cancers that can be subject to diagnosis and/or prognosis using methods of the present invention are listed in Table 12.

TABLE 12

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult |
| Acute Myeloid Leukemia, Adult | (Primary) |
| Acute Myeloid Leukemia, Childhood | Hepatocellular (Liver) Cancer, Childhood |
| Adrenocortical Carcinoma | (Primary) |
| Adrenocortical Carcinoma, Childhood | Hodgkin's Lymphoma, Adult |
| AIDS-Related Cancers | Hodgkin's Lymphoma, Childhood |

TABLE 12-continued

Examples of Cancer Types

AIDS-Related Lymphoma
Anal Cancer
Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sezary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Hodgkin's Lymphoma During Pregnancy
Hypopharyngeal Cancer
Hypothalamic and Visual Pathway Glioma, Childhood
Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sezary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood

TABLE 12-continued

Examples of Cancer Types

| | |
|---|---|
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive Neuroectodermal Tumors, Childhood |
| Soft Tissue Sarcoma, Childhood | |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sezary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

Example 1

Figure 1B:
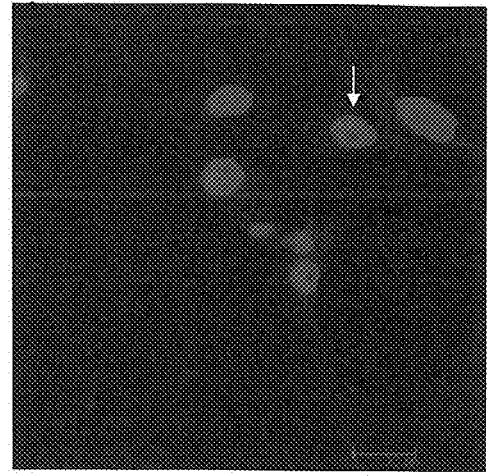

Quantificational and Statistical Analysis of the Differences in Centrosomal Features of Untreated Lung Cancer Cells and Normal Cells Image acquisition. Images useable with the subject invention can be acquired using various techniques and equipment. In one embodiment, centrosomal images were acquired in the Analytic Microscopy Core at the H. Lee Moffitt Cancer Center. A549 lung cancer cells and BEAS 2B normal bronchial epithelial cells were grown in RPMI with 10% FBS and BEGM supplemented with BEGM bullet kit, respectively. Cells were plated and grown on coverslips in a 6-well plate at 37° C. with 5% $CO_2$. Cells were fixed using 4% Paraformaldehyde solution for 30 min at 4° C. and permeabilized using 0.5% Triton X solution. Following blocking with 2% BSA, cells were stained with γ-Tubulin antibody (Sigma). Cells were then incubated with AlexaFluor 594 secondary antibody and mounted using ProLong Antifade with DAPI (Invitrogen). A DMI6000 inverted Leica TCS AOBS SP5 tandem-scanning confocal microscope was used to image the cells, under a 100× oil immersion objective with scanning speed of 100-Hz per each 2048×2048 frame, (FIGS. 1A and 1B). The LAS AF software suite was used to image the cells and compile the max projections from Z-stacks. The acquired image has a resolution of 75.7 nm. Other techniques and equipment can also be used.

Selection of Region of Interest (ROI). In one embodiment, ROIs on an image are selected to include one cell with at least one centrosome. In an exemplified embodiment, a total of 606 untreated cancer ROIs and 57 normal ROIs were selected.

Pre-processing. Although some important centrosomal features of shape are preserved at 75.7 nm resolution, in one embodiment, further resolution enhancement is used. Two dimensional first degree Lagrange interpolation polynomials can also be implemented to enhance the resolution of images (Berrut and Trefethen (2004)). This is a linear interpolation technique which, at any point, uses information given only by the two adjacent pixels and leads to a good approximation of image boundaries. Linear interpolation is performed first in one direction, and then in the other. For example, in order to obtain interpolation at point P, one needs to interpolate at points $R_1$ and $R_2$ using information from $Q_{11}$, $Q_{21}$, and $Q_{12}$, $Q_{22}$, respectively. After that, interpolation at the point P is obtained using the formulae below.

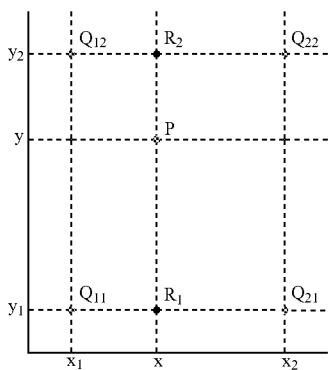

$$f(R_1) = \frac{x_2 - x}{x_2 - x_1} f(Q_{11}) + \frac{x - x_1}{x_2 - x_1} f(Q_{21})$$

$$f(R_2) = \frac{x_2 - x}{x_2 - x_1} f(Q_{12}) + \frac{x - x_1}{x_2 - x_1} f(Q_{22})$$

$$f(P) = \frac{y_2 - y}{y_2 - y_1} f(R_1) + \frac{y - y_1}{y_2 - y_1} f(R_2)$$

Figure 2A:
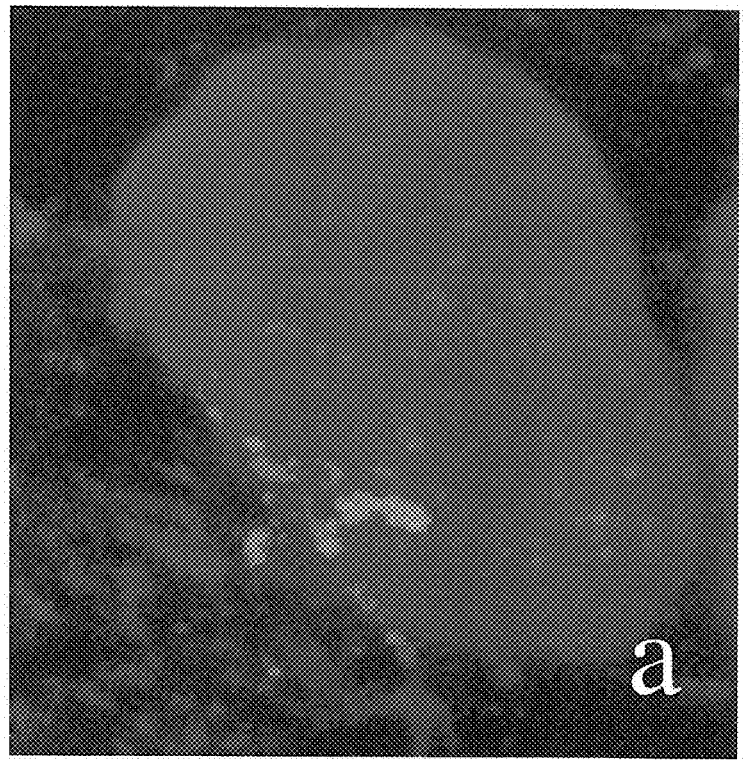
FIGS. 2A and 2B.
Figure 2B:
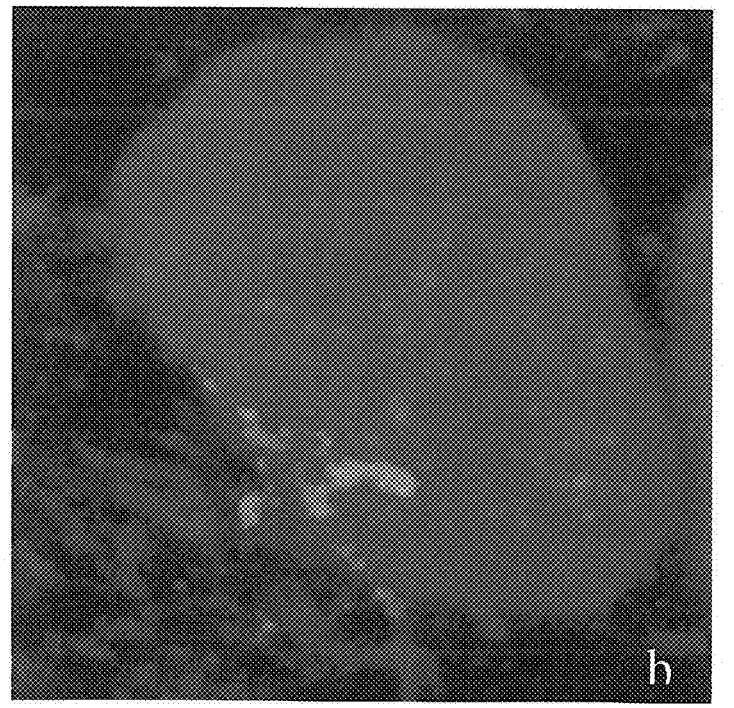
Figure 3A:
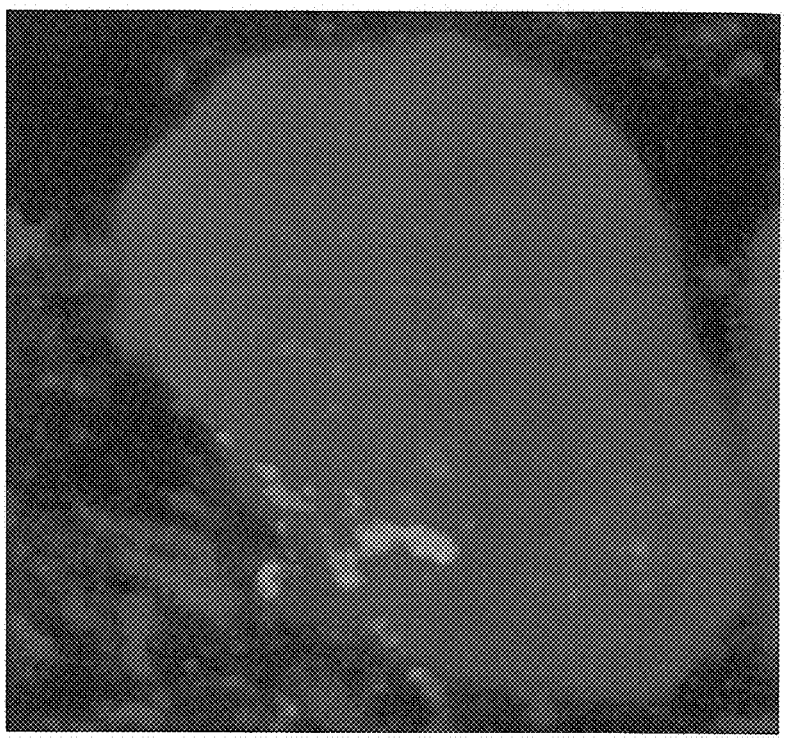
FIGS. 3A-3D.
Figure 3B:
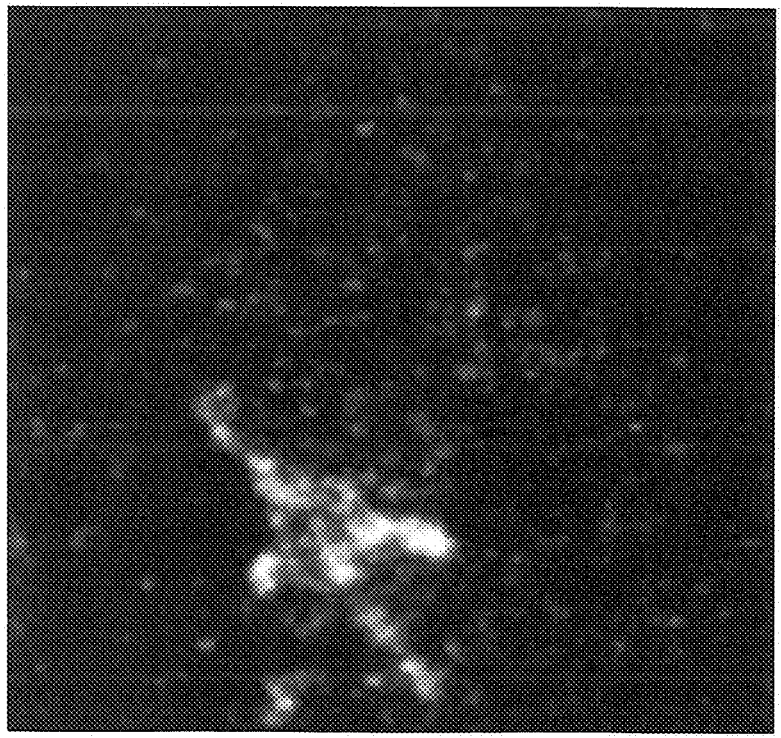
Figure 3C:
Figure 3D:
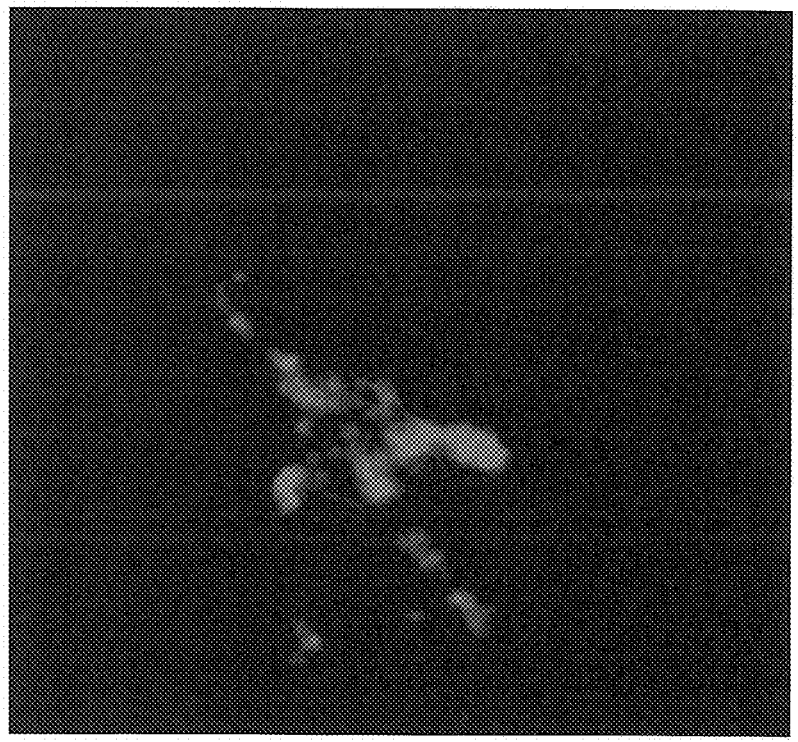
Figure 4A:
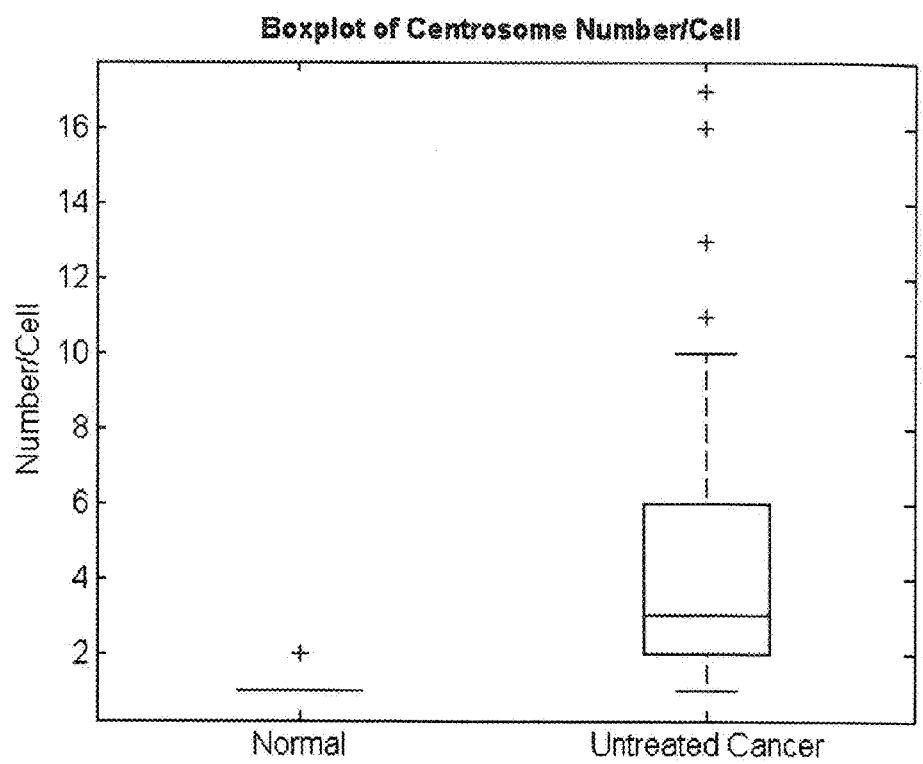
FIGS. 4A-4E show comparisons of centrosomal features between normal and untreated cancer cells. The box plots show the selected 5 features have different medians and different distributions.
Figure 4B:
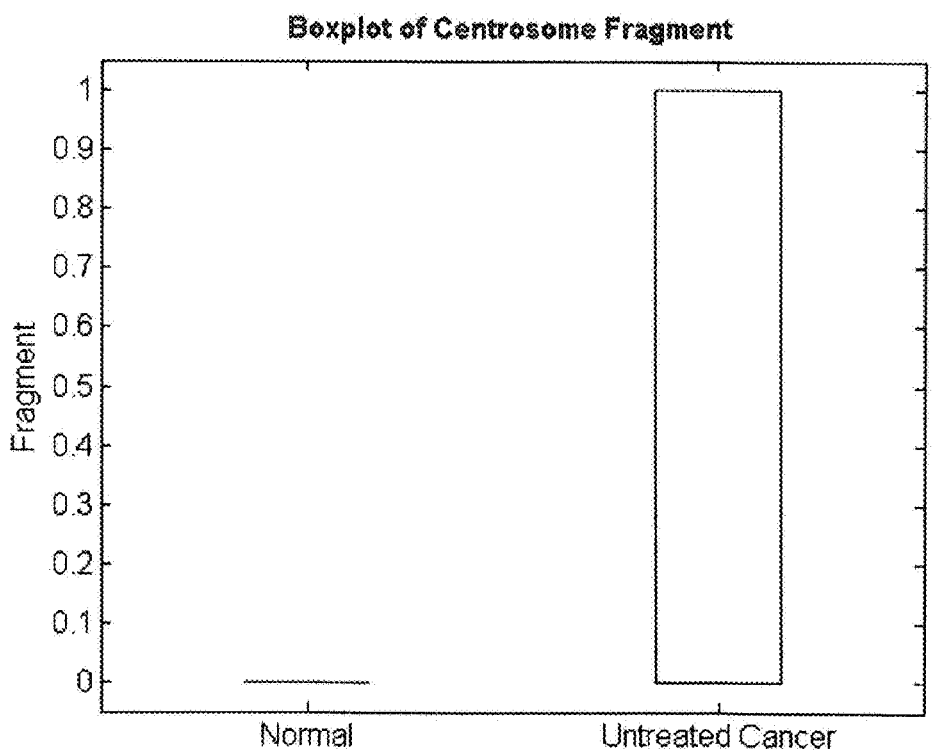
Figure 4C:
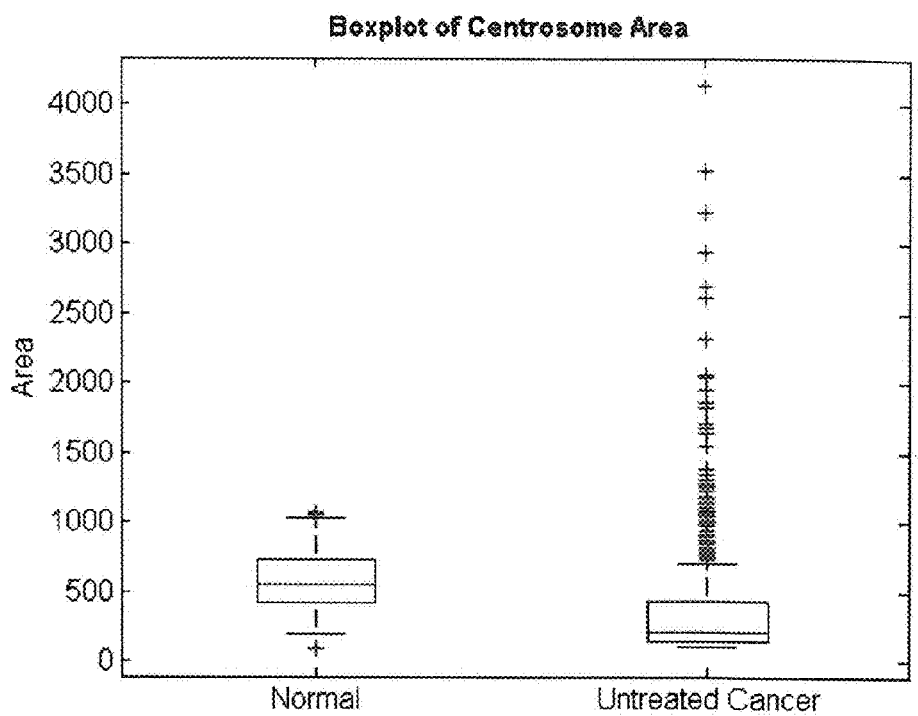
Figure 4D:
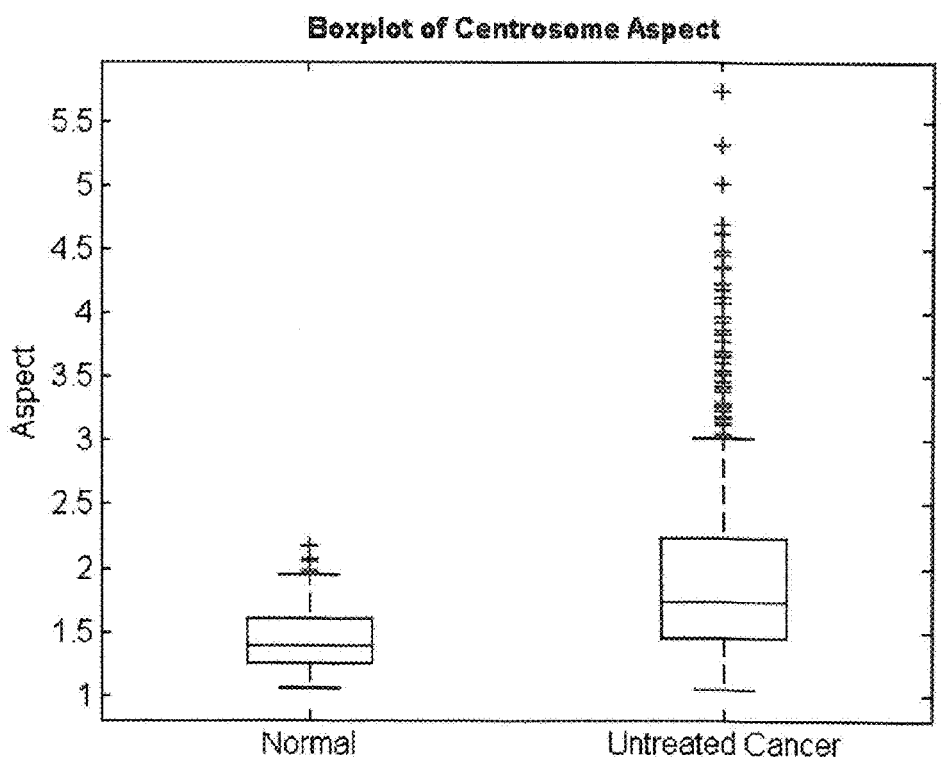
Figure 4E:
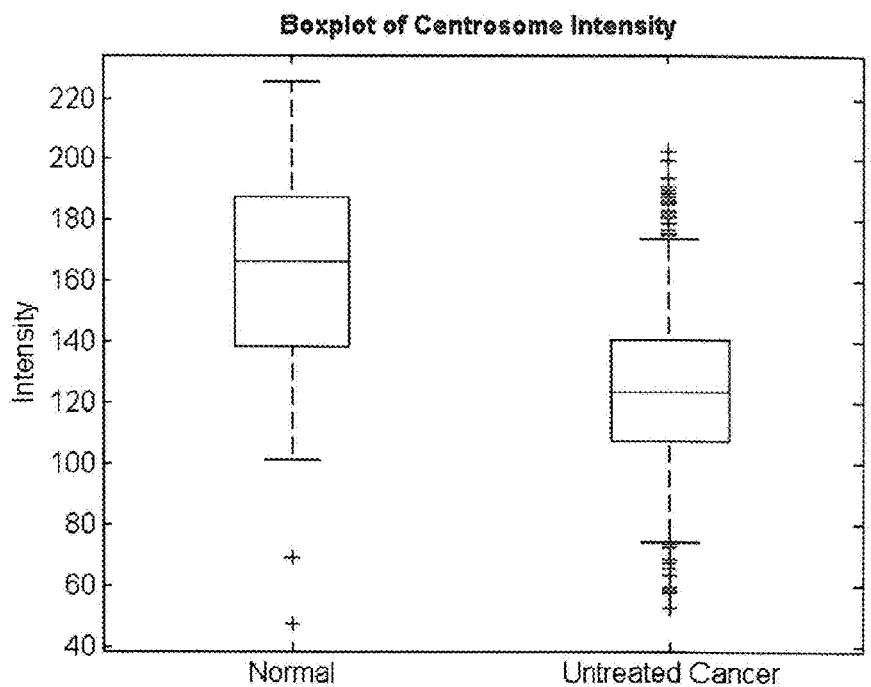
Figure 5A:
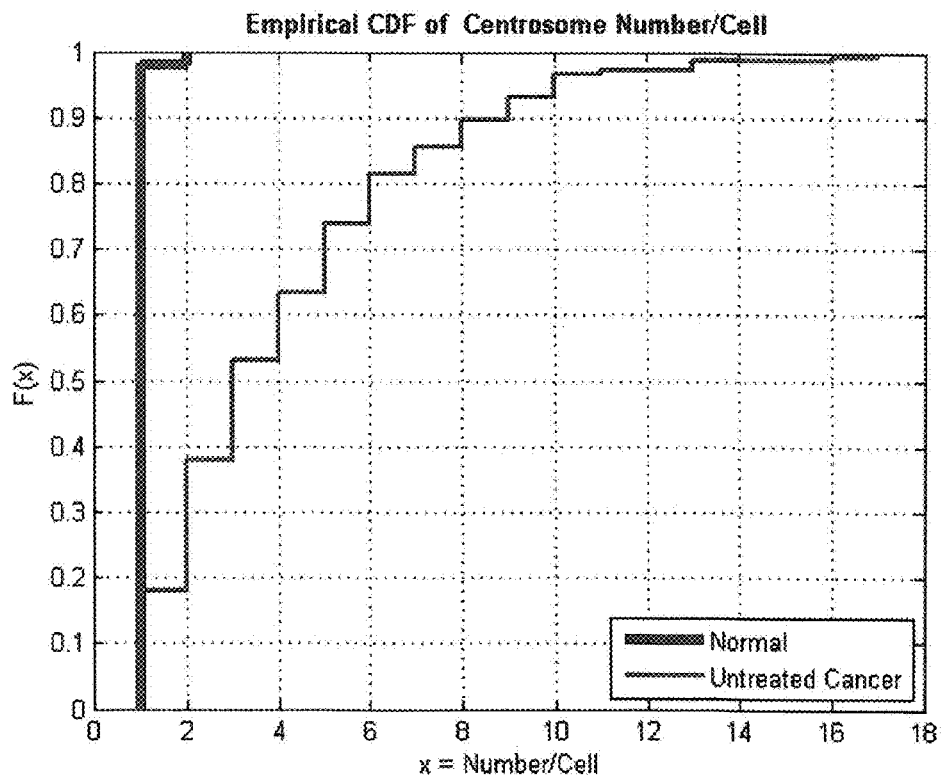
FIGS. 5A-5E show comparisons of Cumulative Distribution Functions (CDF) between normal and untreated cancer centrosomal features. The Empirical CDF plots show the selected 5 features have different distributions.
Figure 5B:
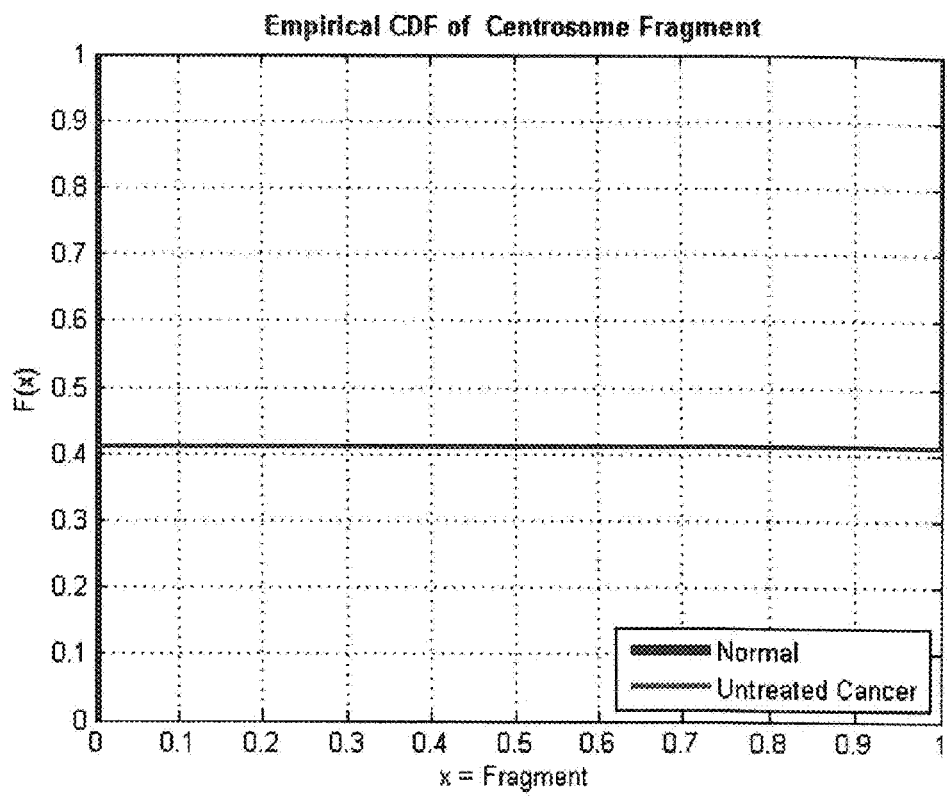
Figure 5C:
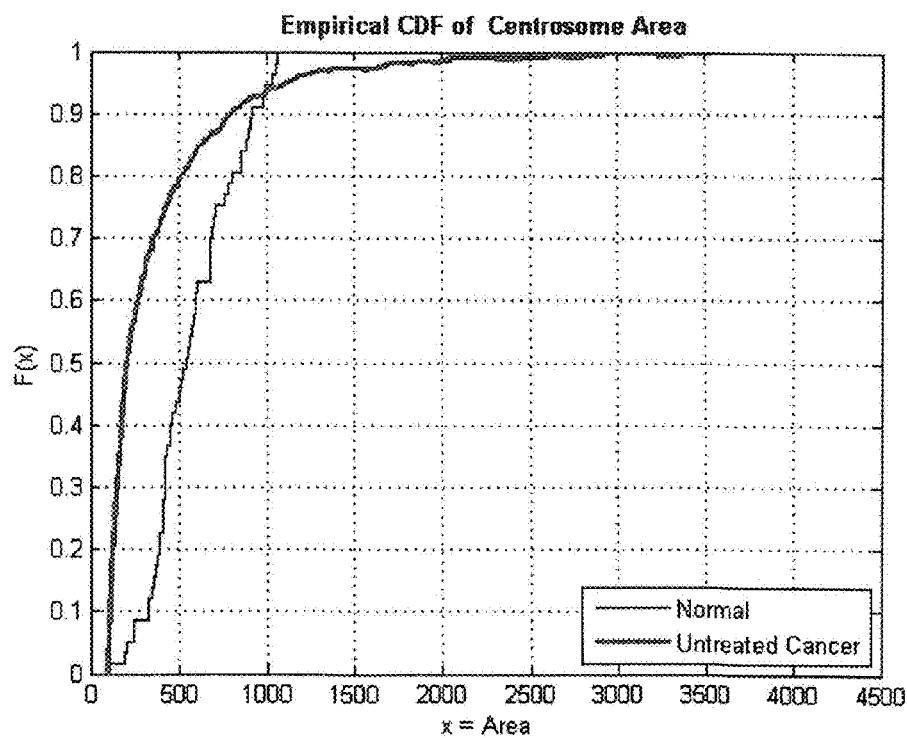
Figure 5D:
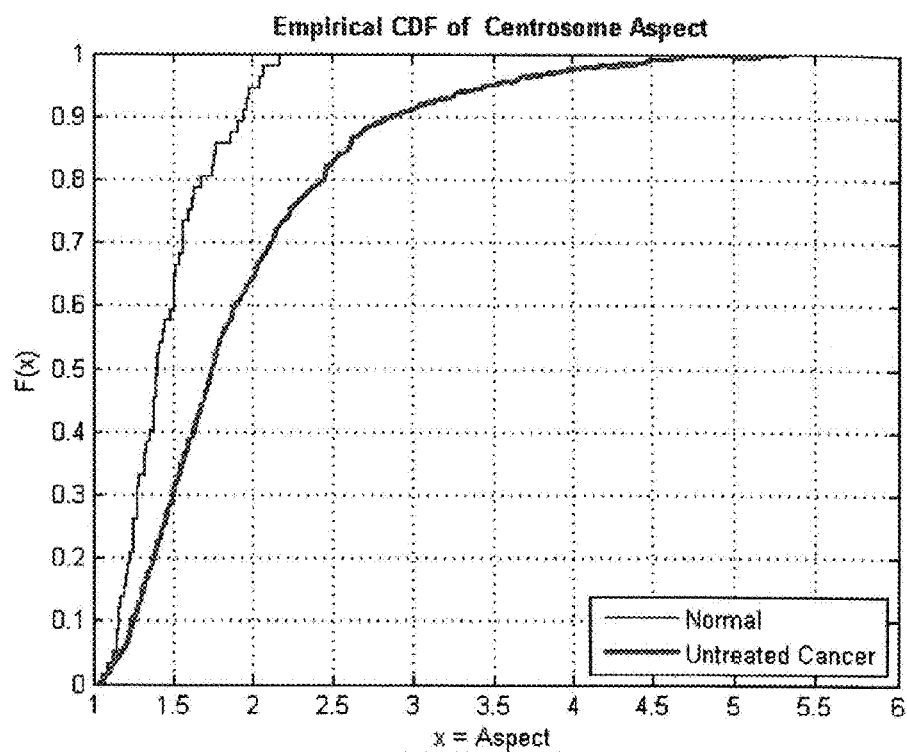
Figure 5E:
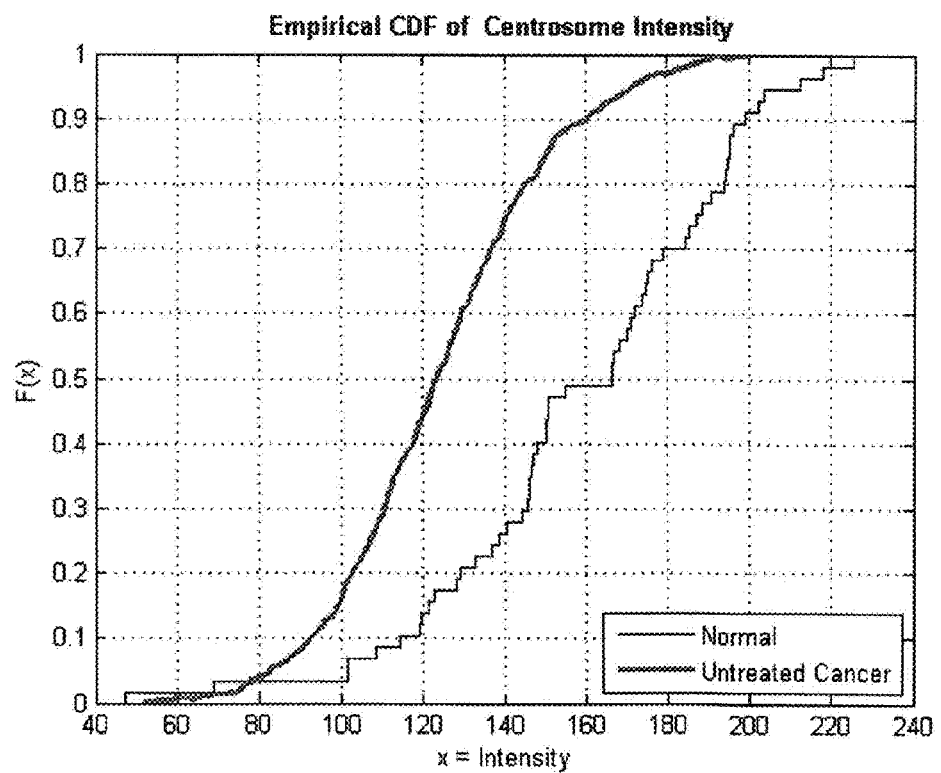

This procedure provides the resolution enhancement which is necessary for successful feature extraction and measurement (see FIGS. 2A and 2B).

Other enhancement techniques can also be used with the present methods. For example, the contrast of the grayscale image I (red channel which includes centrosomal information) could be enhanced by transforming the values using contrast-limited adaptive histogram equalization (CLAHE) (Zuiderveld (1994)).

Image segmentation. Before extracting centrosomal features, the centrosomes can be isolated from other parts of the cells in images (see FIGS. 3A-3D). After comparing various thresholding methods, Kapur's maximum entropy-based thresholding (Yin (2002)) was selected and implemented for this task due to the consistency and accuracy of its outputs. The method considers the foreground (centrosomes) and the background (other parts of the cells) of an image as two different signal sources and finds the threshold which maximizes the sum of the entropies of the two classes as follows.

Let an image have N pixels with gray level ranging from 0 to L-1. Denote by h(i), the number of occurrences of gray level i, and by $P_i$=h(i)/N, the probability of occurrences of gray level i. The method finds threshold t which maximizes $$f(t) = H(0, t) + H(t, L)$$

where $$H(0, t) = -\sum_{i=0}^{t-1} \frac{P_i}{w_0} \ln \frac{P_i}{w_0},$$

$$w_0 = \sum_{i=0}^{t-1} P_i,$$

$$H(t, L) = -\sum_{i=t}^{L-1} \frac{P_i}{w_1} \ln \frac{P_i}{w_1},$$

$$w_1 = \sum_{i=t}^{L-1} P_i.$$

The entropy segmentation threshold depends upon the pixel number of the centrosome space ($P_i$=h(i)/N), and dependents upon the number of channels. From FIGS. 1E and 1F, we can find different distributions of pixel values (histograms) of these two color images. The entropy threshold didn't work well on these color images. We chose not to apply the entropy threshold on a full color image; instead, we applied the entropy threshold on only the red channel because having been stained with AlexaFluor 594, all centrosomal information can be found in this channel. FIGS. 1G and 1H show the red channel histograms of the two region of interest (ROI) images. They have similar distributions with one peak. In fact, all the red channel histograms of centrosome ROI images have similar monotonic distributions. After the optimization procedure, all the thresholds stopped on the right feet of the peaks. We got consistently accurate thresholds.

Features extraction. After centrosomes are separated, centrosomal features can be extracted, which can be later used for discrimination between cancer cells and normal cells. Herein, 11 features are discussed that describe the centrosome from different aspects, which include centrosomal number, size, shape, fragment, and intensity. The following is the definition of the 11 features.

1) Number: Centrosomal number per cell.

$$N = \sum_{k=1}^{max k} \frac{k}{k}$$

Centrolsomal areas are marked as k=111 . . . , 333 . . . , 555 . . . , . . . in a labeled image.

2) Area: The number of pixels in the area of a centrosome.

$$A = \sum_{i=0}^{m-1} \sum_{j=0}^{n-1} \frac{k(i, j)}{k}$$

$$k = 1, 3, 5 \ldots$$

Centrosomal areas are marked as k=111 . . . , 333 . . . , 555 . . . , . . . in a labeled image, k(i, j) is a pixel in the area and has same value with k. Other pixels are marked as 0. m, n are image sizes.

3) Fragment: Defective centrosomes may fragment into multiple microtubule organizing centers (Saunders (2005)).

$$F = \begin{cases} 1 & \text{if there is fragment in a centrosome.} \\ 0 & \text{if there is no fragment in a centrosome.} \end{cases}$$

4) Intensity: An average gray level intensity in a centrosomal area is obtained by adding pixel values over the centrosomal area and then dividing by the area of the centrosome.

$$I = \frac{\sum_{i=0}^{m-1}\sum_{j=0}^{n-1} p_k(i,j)}{\sum_{i=0}^{m-1}\sum_{j=0}^{n-1} \frac{k(i,j)}{k}} \quad k = 1, 3, 5 \ldots$$

Centrosomal areas are marked as k=111 ..., 333 ..., 555 ..., ... in a labeled image, k(i, j) is a pixel in the area and has same value with k. Other pixels are marked as 0. p(i, j) is a gray value in a centrosomal area of a gray image.

5) Intensity standard deviation: The standard deviation of the gray level intensity in the centrosomal area.

$$\sigma = \sqrt{\frac{\sum_{i=0}^{m-1}\sum_{j=0}^{n-1} [p_k(i,j) - I]^2}{A - 1}}$$

A=area (in pixels), I=Intensity p(i, j) is a gray value in a centrosomal area.

6) Area/Box: The ratio between the numbers of pixels in the area of a centrosome and the area of its bounding box. It is always less than or equal to 1.

$$\text{Area/Box} = \frac{\sum_{i=0}^{m-1}\sum_{j=0}^{n-1} \frac{k(i,j)}{k}}{\sum_{i=0}^{m-1}\sum_{j=0}^{n-1} \frac{k(i,j)}{k} + \sum_{i=0}^{m-1}\sum_{j=0}^{n-1} \frac{l(i,j)}{l}} \quad \begin{cases} k = 1, 3, 5 \ldots \\ l = 2, 4, 6 \ldots \end{cases}$$

Centrosomal areas are marked as k=111 ..., 333 ..., 555 ..., ..., in a labeled image, k(i, j) is a pixel in the area and has same value with k. Bounding box areas (not include centrosomal areas) are marked as l=222 ..., 444 ..., 666 ..., ... in a labeled image, l(i, j) is a pixel in the box and has same value with l.

7) Aspect: The ratio between the major axis and the minor axis of the ellipse which is equivalent to a centrosome (has the same area as the centrosome). Aspect is always greater than or equal to 1.

8) Mean Diameter: An average length of the diameters which are drawn through the centrosomal centroid at 2 degree increments.

To find the Mean diameter, we need to find the center of the area first. The Center of an area, which is denoted by Xc, Yc are given by the 1st moment of the object.

$$Xc = \frac{\sum_{i=0}^{m-1}\sum_{j=0}^{n-1} \frac{j \times k(i,j)}{k}}{\sum_{i=0}^{m-1}\sum_{j=0}^{n-1} \frac{k(i,j)}{k}}$$

$$Yc = \frac{\sum_{i=0}^{m-1}\sum_{j=0}^{n-1} \frac{i \times k(i,j)}{k}}{\sum_{i=0}^{m-1}\sum_{j=0}^{n-1} \frac{k(i,j)}{k}}$$

$k = 1, 3, 5 \ldots$ $$\text{Mean diameter} = \frac{\sum_{\theta=0}^{179} d(2\theta)}{180}$$

$d$ – diameter, pass through the center of an area.
$\theta$ – rotation angle

9) Perimeter ratio: The ratio between the convex perimeter of a centrosome and its actual perimeter. Perimeter ratio is always less than or equal to 1.

$$\text{Perimeter ratio} = \frac{\sum_{i=0}^{m-1}\sum_{j=0}^{n-1} \frac{l_1(i,j)}{l_1}}{\sum_{i=0}^{m-1}\sum_{j=0}^{n-1} \frac{l_2(i,j)}{l_2}} \quad \begin{cases} l_1 = 1, 3, 5 \ldots \\ l_2 = 2, 4, 6 \ldots \end{cases}$$

Convex perimeter pixels are marked as $l_1$=111 ..., 333 ..., 555 ..., ..., in a labeled image, $l_1$ (i, j) is a pixel on the convex perimeter and has same value with $l_1$. Perimeter pixels are marked as $l_2$=222 ..., 444 ..., 666 ..., ..., in a labeled image, $l_2$ (i, j) is a pixel on the perimeter and has same value with $l_2$.

10) Roundness: Roundness is equal to the squared perimeter of a centrosome divided by $4\pi A$, where A is the area of the centrosome. Roundness demonstrates how far the shape of the centrosome deviates from a circle. The larger the roundness parameter, the further the deviation of the shape from being round. If a centrosome has a circular shape, its roundness is equal to one, otherwise, it is greater than one.

$$\text{Roundness} = \frac{\left[\sum_{i=0}^{m-1}\sum_{j=0}^{n-1} \frac{l(i,j)}{l}\right]^2}{4\pi \sum_{i=0}^{m-1}\sum_{j=0}^{n-1} \frac{k(i,j)}{k}} \quad \begin{cases} k = 1, 3, 5 \ldots \\ l = 2, 4, 6 \ldots \end{cases}$$

Centrosomal areas are marked as 111 ..., 333 ..., 555 ..., ..., in a labeled image, k(i, j) is a pixel in the area and has same value with k. Boundary areas are marked as 222 ..., 444 ..., 666 ..., ... in a labeled image, l(i, j) is a pixel in the boundary and has same value with l.

11) Fractal dimension (Addison (1997)): The fractal dimension is a measurement of roughness. The rougher the curve, the larger the fractal dimension. The general expression of fractal dimension is $$FD = \lim_{S \to 0} \frac{d(\log(N))}{d(\log(1/S))}$$

where N is the number of hypercubes (for example, square) of side length S required to cover the object (for example, a curve).

In practice, the box counting dimension can be estimated by selecting two sets of [log(N), log(1/S)] coordinates at small value of S. An estimate of Fragment Dimension FD is then given by, $$FD = \frac{\log(N_2) - \log(N_1)}{\log(1/S_2) - \log(1/S_1)}$$
$$= \frac{\log\frac{N_2}{N_1}}{\log\frac{S_1}{S_2}}$$

Other centrosomal features can be used and the features can be extracted, calculated, and/or measured differently. Additional features include, for example, measurement of Consistency/Heterogeneity of individual features (e.g., consistency/heterogeneity of number, area, fragment, intensity, roundness, etc.) among centrosomes within an individual specimen, and consistency/heterogeneity of individual features among centrosomes between different specimens.

For example, centrosomal texture features can be used. To calculate these 13 texture features, first one needs to create a gray-level co-occurrence matrix (GLCM) from a segmented centrosome image. Then calculate 13 texture features from GLCM as follows (Haralick et al. (1973); Haralick and Shapiro (1992)):

Angular second moment
Contrast
Correlation
Sum of squares: Variance
Inverse difference moment
Sum average
Sum variance
Sum entropy
Entropy
Difference variance
Difference entropy
Information measures of correlation
Maximal correlation coefficient (Definitions and formulas can be found from the references).

Elimination of Redundant Features.

In general, one does not need to keep the features which are redundant, i.e., strongly related to other features. If we adopt the correlation between the two variables as the measure of redundancy, we conclude that a feature is useful if it is not highly correlated to any of the other features (Michalak et al. (2006)).

Shape features selection. Six features used to measure centrosomal shape are discussed herein. Correlations between every pair of these six features or other shape features for both normal and untreated cancer cell centrosomes are calculated (Michalak et al. (2006)). In an embodiment, a correlation between two features larger than 0.8 or less than −0.8 is considered to be highly correlated. If no pair of features is highly correlated, no feature is considered redundant, and all of the shape features are used for the centrosome's shape measurement.

Statistical Analysis

Two sample t-test. After centrosome features are selected, the two sample t-test can be performed to verify whether the two samples can be distinguished by these features. The test is carried out under the assumption that the two samples are independent and normally distributed with equal means under the null hypothesis and different means under the alternative hypothesis.

The test result h=1 indicates rejection of the null hypothesis at α=5% significance (95% confidence) level; h=0 indicates failure to reject the null hypothesis. The test returns the p-value p of the test and the confidence interval ci, for the difference of means of the two samples. Although for small sample sizes, centrosome features are not necessarily normally distributed, the central limit theorem guarantees that the sample mean is normally distributed, as long as the sample size is big enough (N≥30). The sample size N=57 and 606 in our study satisfies the requirement. Therefore the two sample t-test is applicable to our data (Terriberry et al. (2005)).

Two sample Kolmogorov-Smirnov test (KS-test). The Kolmogorov-Smirnov test is usually used to determine whether the two samples are drawn from the same distribution (the null hypothesis) or different distributions (the alternative hypothesis). The two-sample KS test is one of the most useful and general nonparametric methods for comparing two samples, as it is sensitive to differences in both location and shape of the empirical cumulative distribution functions of the two samples. The KS-test also has an advantage of making no assumption about the normal distribution of data.

The test result h=1 means rejection of the null hypothesis that distributions of the two samples are the same at α=5% significance (95% confidence) level; the value h=0 indicates failure to reject this hypothesis. The test also returns the p-value p, and the value of the test statistic k which quantifies the difference between distributions of the two samples and can be written as $$k = \text{Max}(|F_1(x) - F_2(x)|)$$

where $F_1(x)$ and $F_2(x)$ are empirical cumulative distribution functions of samples 1 and 2, respectively (Kozmann et al. (1991).

Results. After image acquisition, in total, 606 centrosomes were selected from untreated cancer cells and 57 centrosomes were selected from normal cells. The correlations among centrosomal shape features were calculated to determine feature redundancy. The Number/Cell and Fragment features are different in nature, and different from other features, therefore we preserved Number/Cell and Fragment as independent features. Due to this, we did not calculate correlations between these two features or between these two features and other nine features.

Correlations between the other nine shape features for both the normal cells and untreated cancer cells results are presented in Tables 1 and 2.

Tables 1 and 2 show that centrosome features "Area" and "Mean Diameter" are highly correlated for both normal and untreated cancer cells (correlation coefficient 0.985 and 0.938, respectively), and therefore, one of these features is redundant. "Area" is the only feature which describes centrosome size while "Mean Diameter" is one of six features which describe centrosome shape. Hence, we have removed "Mean Diameter" from further investigation. After "Mean Diameter" is removed, the remaining 10 features are entered into the statistical analysis.

TABLE 1

Correlations between shape features of normal cell centrosomes

|  | Area | Asp | Area/Box | Mean Dia | Rdn | Inten. | Perim ratio | Fract Dim | Inten StDev |
|---|---|---|---|---|---|---|---|---|---|
| Area | 1.000 | −0.005 | −0.319 | 0.985 | 0.496 | 0.067 | −0.304 | 0.370 | 0.283 |
| Asp | −0.005 | 1.000 | −0.497 | 0.074 | 0.514 | −0.261 | −0.294 | 0.246 | −0.257 |
| Area/Box | −0.319 | −0.497 | 1.000 | −0.384 | −0.716 | 0.147 | 0.621 | −0.455 | 0.118 |
| Mean Dia | 0.985 | 0.074 | −0.384 | 1.000 | 0.533 | 0.041 | −0.342 | 0.367 | 0.260 |
| Rdn | 0.496 | 0.514 | −0.716 | 0.533 | 1.000 | −0.126 | −0.695 | 0.750 | −0.068 |
| Inten. | 0.067 | −0.261 | 0.147 | 0.041 | −0.126 | 1.000 | 0.253 | −0.147 | 0.732 |
| Perim ratio | −0.304 | −0.294 | 0.621 | −0.342 | −0.695 | 0.253 | 1.000 | −0.546 | 0.242 |
| Fract Dim | 0.370 | 0.246 | −0.455 | 0.367 | 0.750 | −0.147 | −0.546 | 1.000 | −0.227 |
| Inten StDev | 0.283 | −0.257 | 0.118 | 0.260 | −0.068 | 0.732 | 0.242 | −0.227 | 1.000 |

Asp = Aspect,
Dia = Diameter,
Rdn = Roundness,
Inten = Intensity,
Perim = Perimeter,
Fract = Fractal,
Dim = dimension,
StDev = Standard Deviation

TABLE 2

Correlation between features of untreated cancer cell centrosomes

|  | Area | Asp | Area/Box | Mean Dia | Rdn | Inten. | Perim ratio | Fract Dim | Inten StDev |
|---|---|---|---|---|---|---|---|---|---|
| Area | 1.000 | 0.141 | −0.361 | 0.938 | 0.713 | 0.293 | −0.387 | 0.406 | 0.412 |
| Asp | 0.141 | 1.000 | −0.601 | 0.241 | 0.467 | −0.192 | −0.176 | 0.176 | −0.234 |
| Area/Box | −0.361 | −0.601 | 1.000 | −0.435 | −0.714 | 0.229 | 0.564 | −0.569 | 0.235 |
| Mean Dia | 0.938 | 0.241 | −0.435 | 1.000 | 0.698 | 0.347 | −0.423 | 0.377 | 0.477 |
| Rdn | 0.713 | 0.467 | −0.714 | 0.698 | 1.000 | −0.099 | −0.673 | 0.729 | −0.051 |
| Inten. | 0.293 | −0.192 | 0.229 | 0.347 | −0.099 | 1.000 | 0.132 | −0.220 | 0.699 |
| Perim ratio | −0.387 | −0.176 | 0.564 | −0.423 | −0.673 | 0.132 | 1.000 | −0.744 | 0.138 |
| Fract Dim | 0.406 | 0.176 | −0.569 | 0.377 | 0.729 | −0.220 | −0.744 | 1.000 | −0.210 |
| Inten StDev | 0.412 | −0.234 | 0.235 | 0.477 | −0.051 | 0.699 | 0.138 | −0.210 | 1.000 |

Asp = Aspect,
Dia = Diameter,
Rdn = Roundness,
Inten = Intensity,
Perim = Perimeter,
Fract = Fractal,
Dim = dimension,
StDev = Standard Deviation The two sample t-test comparison between normal and untreated cancer centrosomes returned p-values less than 0.001 for all 10 features. Correspondingly, the 99.9% confidence intervals (ci) on the mean differences of all 10 features do not contain zero. This statistical result rejects the null hypothesis, i.e., H=1 for all 10 features (see Table 3). Based on the statistical test result, we can say with 99.9% confidence that for all 10 features there are significant mean differences between normal and untreated cancer centrosomes.

The difference in the distributions of centrosomal features for normal and untreated cancer cells can be also seen from the box plots below. We present box-plots for five centrosomal features: centrosomal number, size, fragment, intensity, and shape. From FIGS. 4A-4E, we can see that these five features have different medians and, overall, different distributions. The other five box plots show a similar pattern.

The two sample Kolmogorov-Smirnov test confirmed the boxplot results and are consistent with the two-sample t-test (see Table 4). The test verifies that all 10 centrosome features have different distributions for the normal and untreated cancer cells (h=1). The largest p-value is 0.00015 which means that with 99.985% confidence we can claim that distribution of every feature is different for two types of cells. The test also returns the values of statistic k that indicates whether the distances between cumulative distribution functions (CDFs) are sufficiently large to be distinct. The smallest value of k is 29.5% which indicates that the distances between CDFs of the centrosome features for normal and untreated cancer cells are large enough to distinguish them.

We illustrate the CDF plots of 5 centrosomal features (see FIGS. 5A-5E): centrosomal number, size, fragment, intensity, and shape. One can see substantial differences between the shapes and positions of the CDF curves for centrosomal features of normal and untreated cancer cells. It is also apparent that the maximum distances (k) between pairs of curve are quite large. This means that all pairs of samples have different distributions and came from different populations. The remaining five CDF curves show a similar pattern.

Thus, the present invention can be used to distinguish untreated cancer cells from normal cells through quantitative analyses of centrosomal features. In an embodiment, cancer can thus be diagnosed according to this method.

TABLE 3

Two Sample t-test result for Normal and Untreated cancer cells

| | Num/Cell | Frag. | Area | Asp | Area/Box | Rdn | Perim (ratio) | Fract Dim | Inten. | Inten StDev |
|---|---|---|---|---|---|---|---|---|---|---|
| h | 1 | 1 | 1 | 1 | 1 | 1 | 1 | 1 | 1 | 1 |
| p | 0.000e−003 | 0.000e−003 | 0.622e−003 | 0.001e−003 | 0.000e−003 | 0.206e−003 | 0.396e−003 | 0.000e−003 | 0.000e−003 | 0.001e−003 |
| ci | −3.986 | −0.719 | 86.693 | −0.681 | 0.054 | −0.786 | 0.011 | −0.046 | 26.536 | −3.888 |
| | −2.337 | −0.461 | 317.54 | −0.294 | 0.117 | −0.244 | 0.039 | −0.021 | 41.295 | −1.700 |

Num = Number,
Frag = Fragment,
Asp = Aspect,
Rdn = Roundness,
Inten = Intensity,
Perim = Perimeter,
Fract = Fractal,
Dim = dimension,
StDev = Standard Deviation

TABLE 4

Two-sample Kolmogorov-Smirnov test for Normal and Untreated Cancer cells

| | Num/Cell | Frag. | Area | Asp | Area/Box | Rdn | Perim (ratio) | Fract Dim | Inten | Inten StDev |
|---|---|---|---|---|---|---|---|---|---|---|
| h | 1 | 1 | 1 | 1 | 1 | 1 | 1 | 1 | 1 | 1 |
| p | 4.976e−024 | 2.547e−013 | 3.626e−016 | 8.107e−008 | 2.789e−008 | 1.052e−006 | 1.597e−004 | 2.213e−008 | 1.046e−012 | 1.662e−005 |
| k | 0.803 | 0.590 | 0.579 | 0.397 | 0.409 | 0.366 | 0.295 | 0.412 | 0.511 | 0.329 |

Num = Number,
Frag = Fragment,
Asp = Aspect,
Rdn = Roundness,
Inten = Intensity,
Perim = Perimeter,
Fract = Fractal,
Dim = dimension,
StDev = Standard Deviation Discussion Described herein is an objective procedure for characterizing and quantifying centrosomal defects found in lung cancer cells, but that are not found in normal cells. The term 'centrosome amplification' is commonly used to signify centrosomes that subjectively appear significantly larger than normal (as defined by the specific staining of structural centrosome components in excess of that seen in the corresponding normal tissue or cell type); supernumerary centrioles (more than four) in centrosomes; inverted polarity of centrosome location; and/or more than two centrosomes are present within a cell. Amplified centrosomes also show protein hyperphosphorylation and altered functional properties such as an increased microtubule nucleating capacity (D'Assoro et al. (2008); Salisbury et al. (2004); Hontz et al. (2007)). These structural centrosome abnormalities have been implicated as potential cause of loss of cell and tissue architecture seen in cancer (i.e., anaplasia) through altered centrosome function, and resulting in chromosome missegregation during mitosis as a consequence of multipolar spindle formation (Piel et al. (2001)).

Until now, researchers commonly detect the centrosome defects through microscopy. Guo et al. have done limited image analysis of centrosomal features, which include numerical and structural centrosome amplification. The cell was considered to have structural centrosome amplification if the diameter of its centrosome was greater than twice the diameter of the normal centrosome and/or if the shape of its centrosome became irregular (Guo et al. (2007)). These investigators applied semi-quantitative image analysis of cells. Other approaches for quantitation of centrosome abnormalities have used semi-quantitative microscopy based procedures that cannot practically avoid subjective judgment even with highly-experienced microscopists.

The novel quantitative analysis and statistical inference of centrosomal features, extracted from cell images using the subject invention avoids those pitfalls and provides objective assessment of centrosome features. The methods include quantitative measurement of a centrosome features profile, capable not only of detecting feature differences, but also of showing the magnitude and consistency of these differences. The diameter is not sufficient to characterize the structure or shape of a centrosome. In one embodiment, five features have been used in the research herein to describe the centrosome shape representing non-correlated aspects of centrosome morphology. Corresponding statistical analysis of centrosome features show the significant differences of quantitatively measured features between normal and cancer centrosomes. Therefore, the present invention can be used to distinguish untreated cancer cells from normal cells through quantitative analysis of centrosomal features. Quantitative calculation and analysis of centrosomal features can also serve as a marker for monitoring and/or predicting cancer progression as discussed herein.

Example 2

Discriminant and Prognosis of Stage I Long-Term and Short-Term Survival Lung Cancer Patients Through Quantitative Analysis of Centrosomal Features Tissue Processing and Immunohistochemisty 35 cases of lung tissue with different forms and stage of cancer were provided from H. Lee Moffitt Cancer Center & Research Institute. Samples were processed within the Moffitt Microarray Core. Tissues were fixed in formaldehyde, and then embedded in paraffin. For immunohistochemistry, sections were deparafinized using xylene and ethanol washes followed by antigen retrieval buffer (Dako). According to protocol, sections were washed in PBS then blocked (10% normal goat serum, 3% BSA and 0.5% gelatin in PBS) for 1 hour at 4C. Sections were incubated overnight at 4C in primary antibody anti-gamma Tubulin, produced in rabbit (Sigma, 1:300 diluted in PBS with 2% Normal Goat Serum. Sections were washed in PBS-T, incubated with secondary antibody AlexaFlour 633 goat anti-rabbit IgG (Invitrogen, 1/200) for 1 hour, then rinsed in PBS-T. Sections were counter-stained and mounted with Prolong Antifade solution w/DAPI (Invitrogen).

Image Acquisition

Figure 6A:
FIGS. 6A-6E.
Figure 6B:
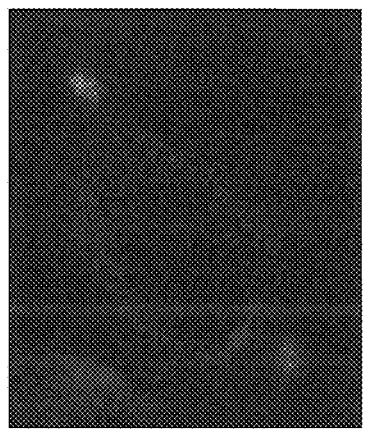
Figure 6C:
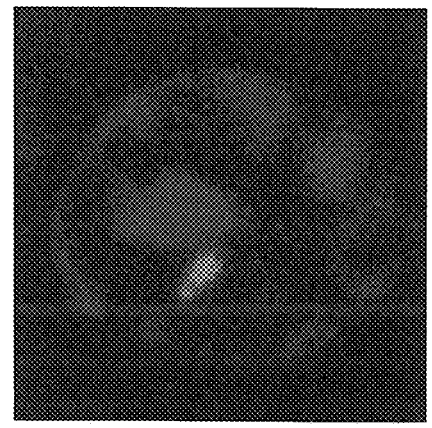
Figure 6D:
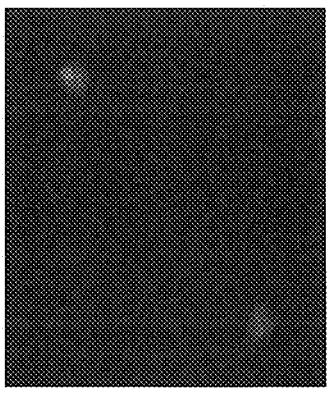
Figure 6E:
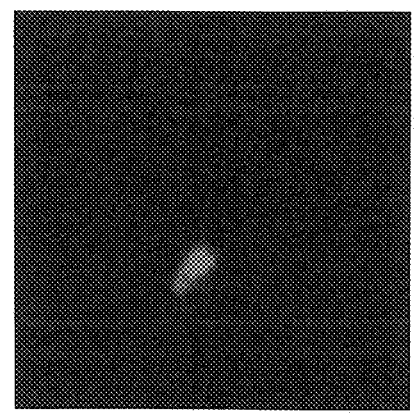

Centrosomal images were acquired in the Analytic Microscopy Core at the H. Lee Moffitt Cancer Center. A DMI6000 inverted Leica TCS AOBS SP5 tandem-scanning confocal microscope was used to image the tissue, under a 100× oil immersion objective with scanning speed of 100-Hz per each 2048×2048 frame. The LAS AF software suite was used to image the tissue and compile the max projections from Z-stacks. The acquired image has a resolution of 75.7 nm (see FIG. 6A).

Among the 35 cases which are totally scanned were six stage 1 NSCLC survivors (followed for nine years or more) and nine fatalities who survived four years or less. Of these stage 1 cases, six of the nine-year or more survivors and six cases who died after four-years or less are used for discriminant analysis. Among the 12 cases, nine-year or more survival cases consist of four cases of stage 1A and two cases of stage 1B lung cancer; four-year or less survival cases consist of three cases of stage 1A and three cases of stage 1B lung cancer.

Figure 1C:

A Region of Interest (ROI) is selected to consist of one cell with at least one centrosome (see FIGS. 1B and 1C). In total, 211 ROIs with 309 centrosomes from four-year or less survival cases and 235 ROIs with 594 centrosomes from nine-year or more survival cases have been acquired for this experiment.

Image Processing

Image Enhancement

Since the centrosome is a very small cellular organelle, 75.7 nm resolution is generally not satisfactory to distinguish centrosome features, such as shape, boundary and structure analysis. Enhancement has been performed to further increase ROI images' resolution. Two dimensional first degree Lagrange polynomial interpolation (Berrut and Trefethen (2004)) is implemented to enhance resolution of the images. This is a linear interpolation technique which, at any point, uses information given only by the two adjacent pixels and leads to a good image approximation.

Image Segmentation

After enhancement and before extracting centrosomal features, the centrosomes need to be isolated from other parts (background) of the cell images. After comparing various thresholding methods, Kapur's maximum entropy-based thresholding (Yin (2002)) was selected and implemented for this task due to the consistency and accuracy of its outputs. The method considers the foreground (centrosomes) and the background (other parts of the cells) of an image as two different signal sources and finds the threshold which maximizes the sum of the entropies of the two classes as follows.

Let an image have N pixels with gray level ranging from 0 to L-1. Denote by h(i), the number of occurrences of gray level i, and by $P_i$=h(i)/N, the probability of occurrences of gray level i. The method finds threshold t which maximizes $$f(t) = H(0, t) + H(t, L)$$

where $$H(0, t) = -\sum_{i=0}^{t-1} \frac{P_i}{w_0} \ln \frac{P_i}{w_0},$$

$$w_0 = \sum_{i=0}^{t-1} P_i,$$

$$H(t, L) = -\sum_{i=t}^{L-1} \frac{P_i}{w_1} \ln \frac{P_i}{w_1},$$

$$w_1 = \sum_{i=t}^{L-1} P_i.$$

Figure 1D:
Figure 1E:
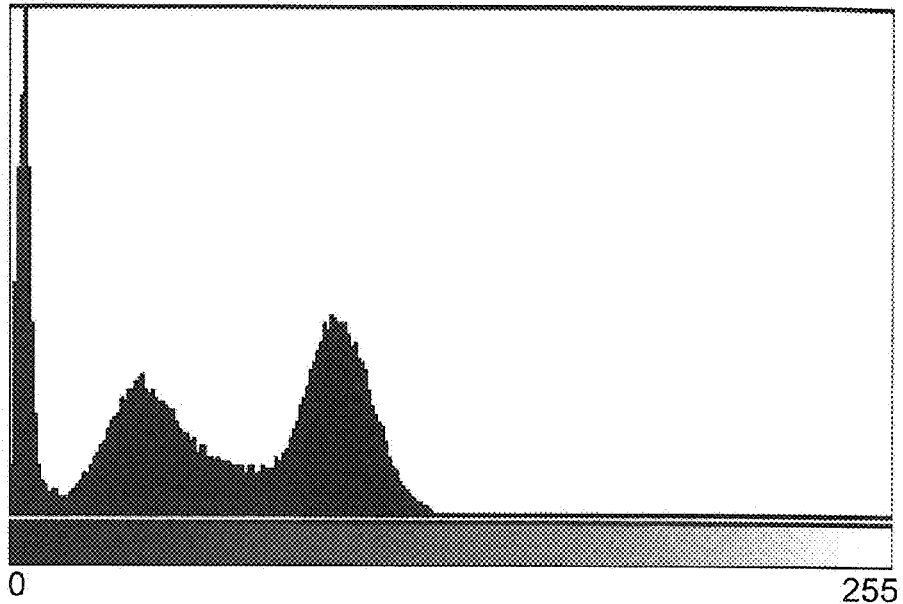
Figure 1F:
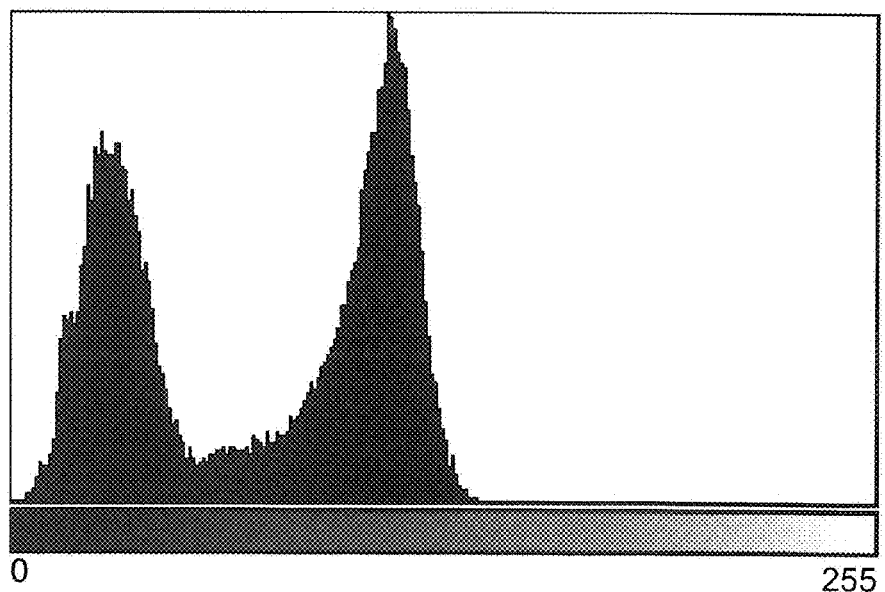
Figure 1G:
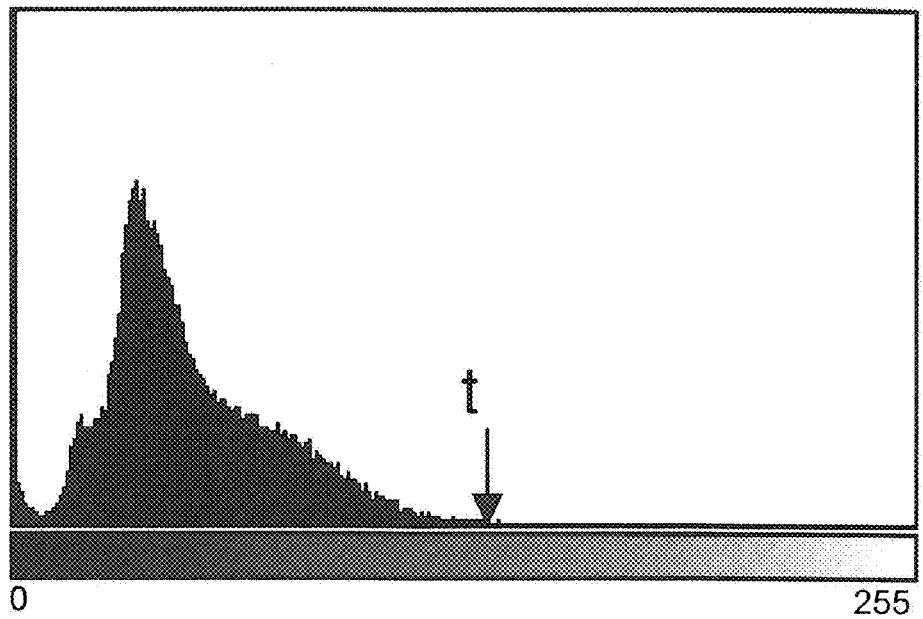
Figure 1H:
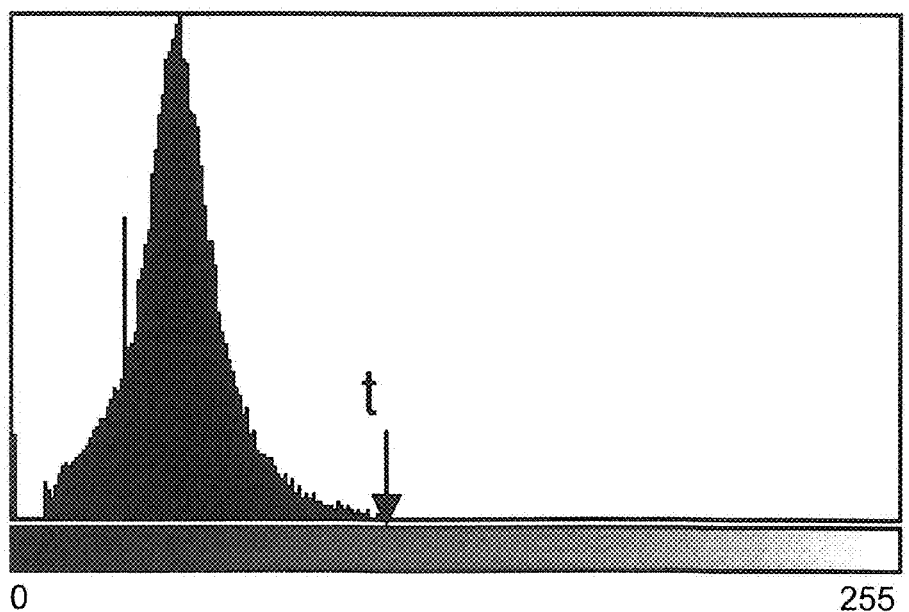

The entropy threshold got consistently accurate segmentation (see FIGS. 1D and 1E).

Feature Extraction and Optimization

Feature Extraction

After centrosomes are isolated, 12 specific centrosomal features are extracted, to be later used for discrimination between long term and short term survival cases. The definitions of these 12 features are as following:

(1) Number—Number of centrosomes per cell.
(2) Area—The number of pixels in the area of a centrosome.
(3) Area/Box—The ratio between the numbers of pixels in the area of a centrosome and the area of its bounding box. It is always less than or equal to 1.
(4) Aspect—The ratio between the major axis and the minor axis of the ellipse which is equivalent to a centrosome (has the same area as the centrosome). Aspect is always greater than or equal to 1.
(5) Hole Ratio—Ratio of centrosomal area excluding holes to total area of centrosome.
(6) Perimeter ratio—The ratio between the convex perimeter of a centrosome and its actual perimeter. Perimeter ratio is always less than or equal to 1.
(7) Roundness—Roundness is equal to the squared perimeter of a centrosome divided by $4\pi A$, where A is the area of the centrosome. Roundness demonstrates how far the shape of the centrosome deviates from a circle. The larger the roundness parameter, the further the deviation of the shape from being round. If a centrosome has a circular shape, its roundness is equal to one, otherwise, it is greater than one.
(8) Fractal dimension (Addison (1997))—The fractal dimension is a measurement of roughness. The rougher the curve, the larger the fractal dimension. The general expression of fractal dimension is $$FD = \lim_{S \to 0} \frac{d(\log(N))}{d(\log(1/S))}$$

where N is the number of hypercubes (for example, square) of side length S required to cover the object (for example, a curve).

In practice, the box counting dimension can be estimated by selecting two sets of [log(N), log(1/S)] coordinates at small value of S. An estimate of Fragment Dimension FD is then given by, $$FD = \frac{\log(N_2) - \log(N_1)}{\log(1/S_2) - \log(1/S_1)}$$

$$= \frac{\log \frac{N_2}{N_1}}{\log \frac{S_1}{S_2}}$$

(9) Intensity—An average gray level intensity in a centrosomal area is obtained by adding pixel values over the centrosomal area and then dividing by the area of the centrosome.

(10) Intensity standard deviation—The standard deviation of the gray level intensity in the centrosomal area.

(11) Solidity—The proportion of the pixels in the convex hull that are also in the region. Computed as Area/ConvexArea.

(12) Eccentricity—The eccentricity is the ratio of the distance between the foci of the ellipse and its major axis length. The value is between 0 and 1. (0 and 1 are degenerate cases; an ellipse whose eccentricity is 0 is actually a circle, while an ellipse whose eccentricity is 1 is a line segment.)

These 12 features can be classified into six categories:

I. Centrosome Number: Number/Cell,
II. Centrosome Size: Area.
III. Centrosome Shape: Aspect, Area/Box, Roundness, Perimeter Ratio, Solidity, and Eccentricity.
IV. Centrosome Boundary: Fractal Dimension.
V. Centrosome Structure: Hole Ratio.
VI. Centrosome Intensity: Mean Intensity and Intensity Standard Deviation.

Feature Selection and Optimization

Feature selection or feature set optimization is a critical issue in discriminant analysis or classification. The purpose of feature selection is: 1) Feature set reduction to reduce the computation and 2) Reduction of noise to improve the classification accuracy. Feature selection algorithms can be roughly grouped into two categories: filter methods and wrapper methods. Filter methods rely on general characteristics of the data without involving the chosen learning algorithm. Wrapper methods use the performance of the chosen learning algorithm to evaluate each candidate feature subset. Peng et al. developed a feature selection algorithm called "minimum redundancy—maximum relevance (MRMR) feature selection" (Peng et al. (2005); Ding and Peng (2005)). MRMR is a filter method. This method selects features by testing whether some preset conditions about the features and the target class are satisfied. It often yields comparable classification errors and high generalization of the selected features for different classifiers with low cost of computation. MRMR provides a more balanced coverage of the space and capture broader characteristics of phenotypes.

Mutual information is a measure of relevance of classes. Bigger difference for difference classes should have larger mutual information. Given two random variables x and y, their mutual information is defined based on their joint probabilistic distribution p(x, y) and density functions p(x), p(y).

$$I(x, y) = \sum_{i,j} p(x_i, y_j) \log \frac{p(x_i, y_j)}{p(x_i)p(y_j)} \text{ for discrete variables}$$

$$I(x, y) = \int \int p(x_i, y_j) \log \frac{p(x_i, y_j)}{p(x_i)p(y_j)} dx dy \text{ for continous variables}$$

The minimum redundancy condition is:

$$\min W_I, \quad (5)$$

$$W_I = \frac{1}{|S|^2} \sum_{i,j \in S} I(x_i, x_j)$$

where |S| is the number of features in S.
The maximum relevance condition is:

$$\max V_I, \quad (6)$$

$$V_I = \frac{1}{|S|^2} \sum_{i \in S} I(x_i, c)$$

where c is the target class.

The MRMR feature set is obtained by optimizing the two conditions simultaneously. The order of our original 12 features are:

| 1 | 2 | 3 | 4 | 5 | 6 | 7 | 8 | 9 | 10 | 11 | 12 |
|---|---|---|---|---|---|---|---|---|----|----|----|
| Num/cell | Area | Aspect | Area/Box | Hole Ratio. | Roundness | Inten. | Perim. Ratio | Fractal Dimen. | Inten. Stdev. | Solidity | Eccentricity |

The optimized order by MRMR is:

| 9 | 6 | 2 | 1 | 8 | 7 | 3 | 5 | 4 | 12 | 10 | 11 |
|---|---|---|---|---|---|---|---|---|----|----|----|

Figure 7:
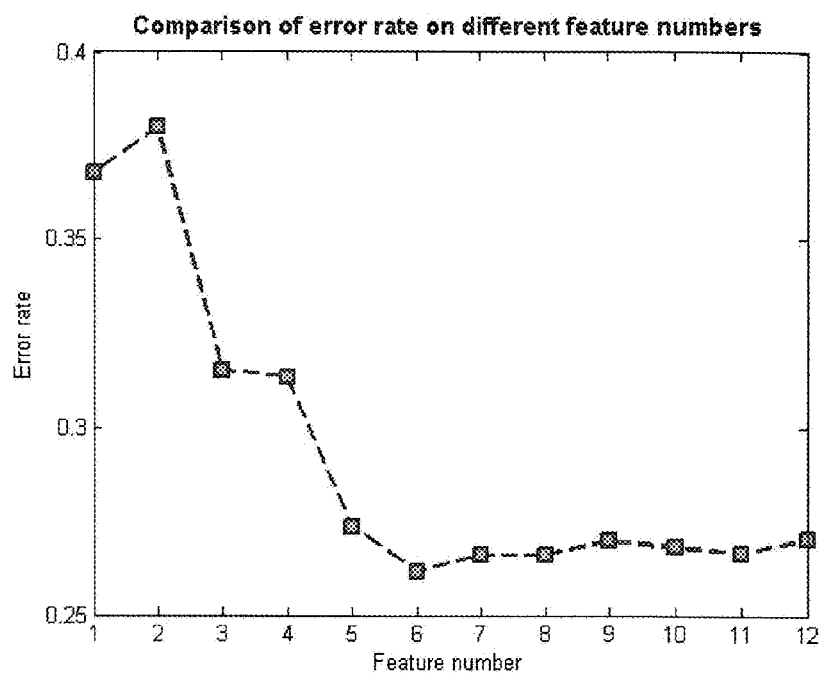
FIG. 7. The distribution of error rates reveals the variation of error rates by feature number. The order of features is optimized by minimum redundancy—maximum relevance (MRMR) (Peng et al. (2005); Ding and Peng (2005)). It shows the error rate reaching the minimum when the feature number is six.
Figures 8A, 8B:
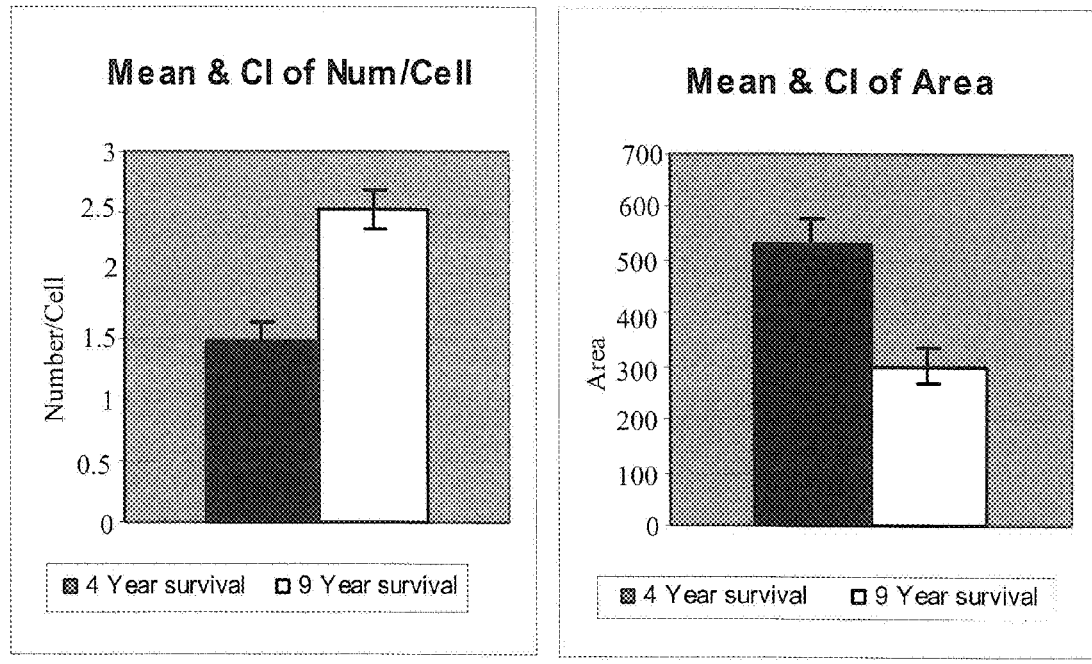
FIGS. 8A-8F show comparisons of mean and confidence interval for Stage I NSCLC patients who survived 4 years (fatalities) and those who survived 9 years (survivors). For all six features, there are obvious differences between the means and there is no overlap for their confidence intervals.
Figure 8C:
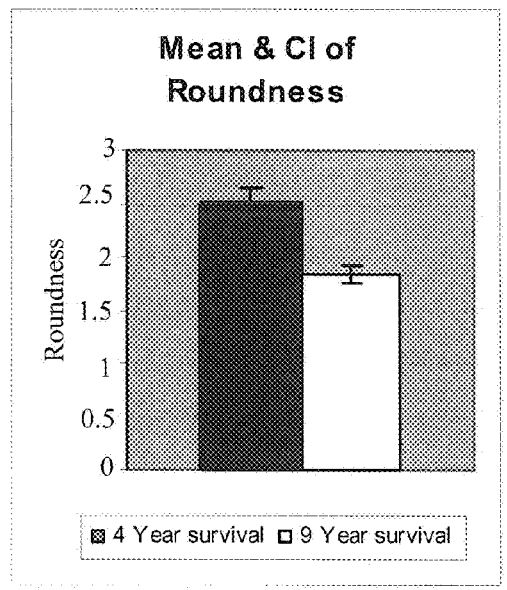
Figure 8D:
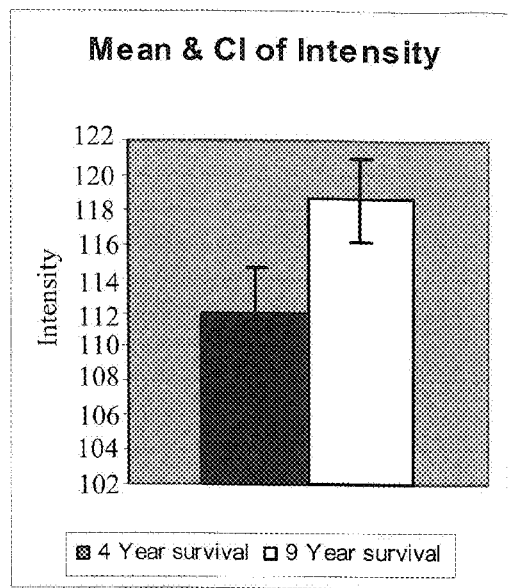
Figure 8E:
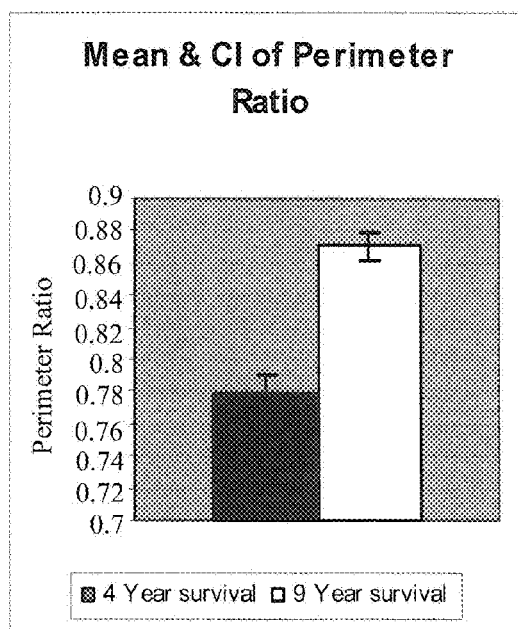
Figure 8F:
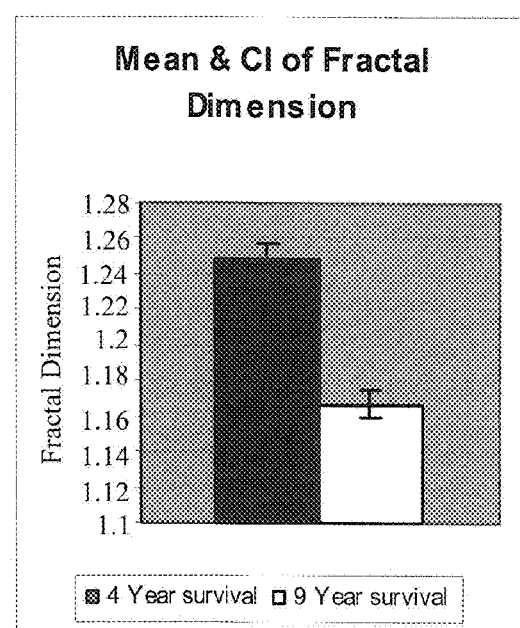
Figure 9A:
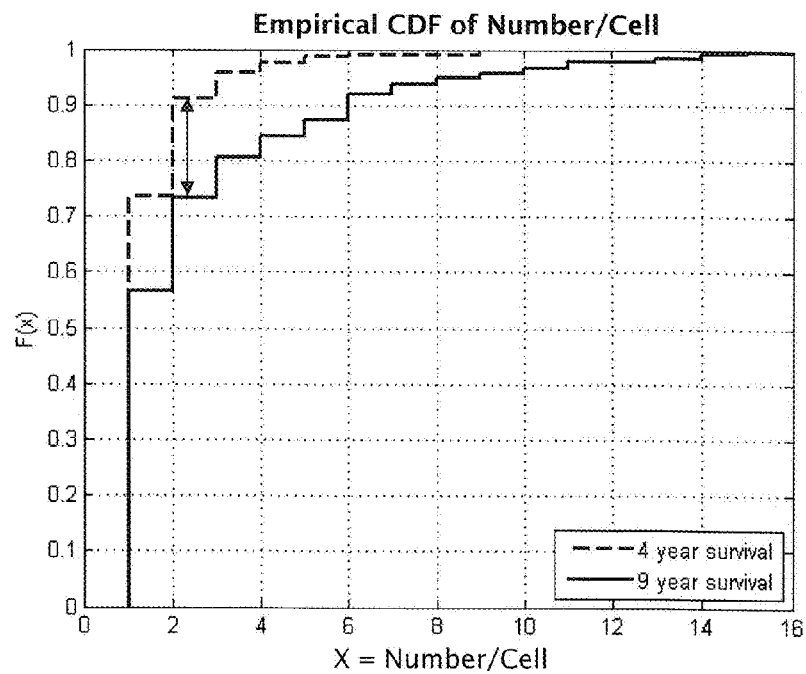
FIGS. 9A-9F show comparison of distribution (location and shape) for 4-year (fatality) and 9-year (survivor) patients. For all six features, the six features have different distributions.
Figure 9B:
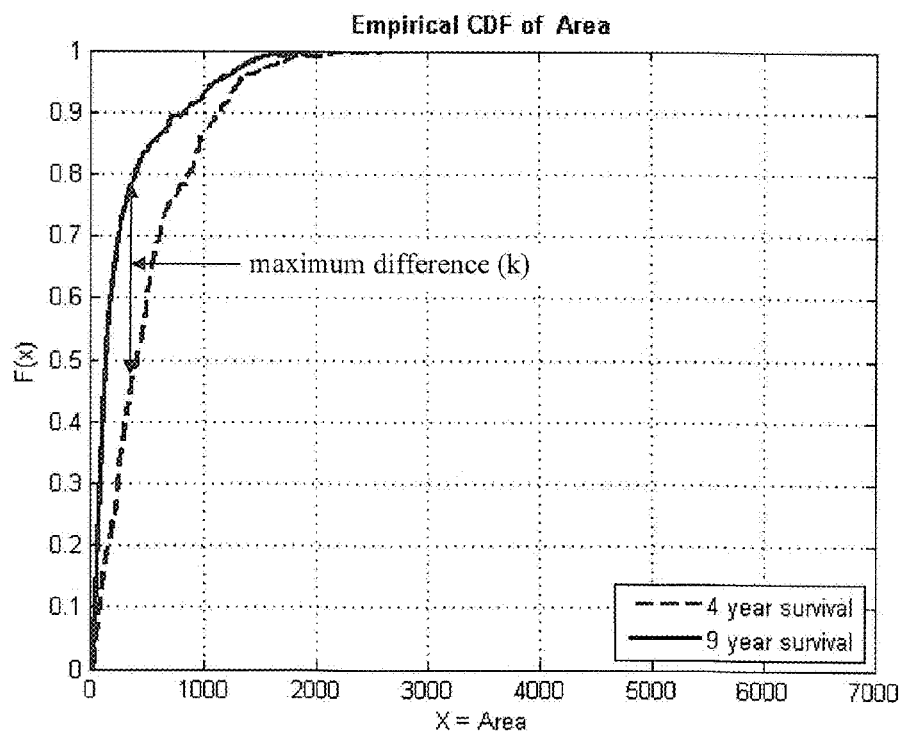
Figure 9C:
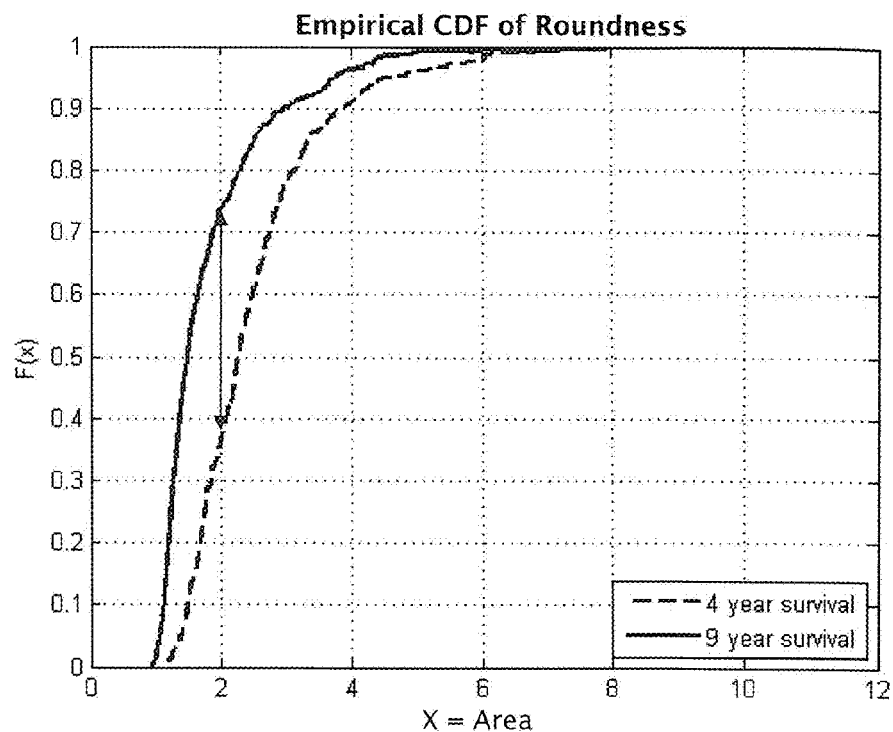
Figure 9D:
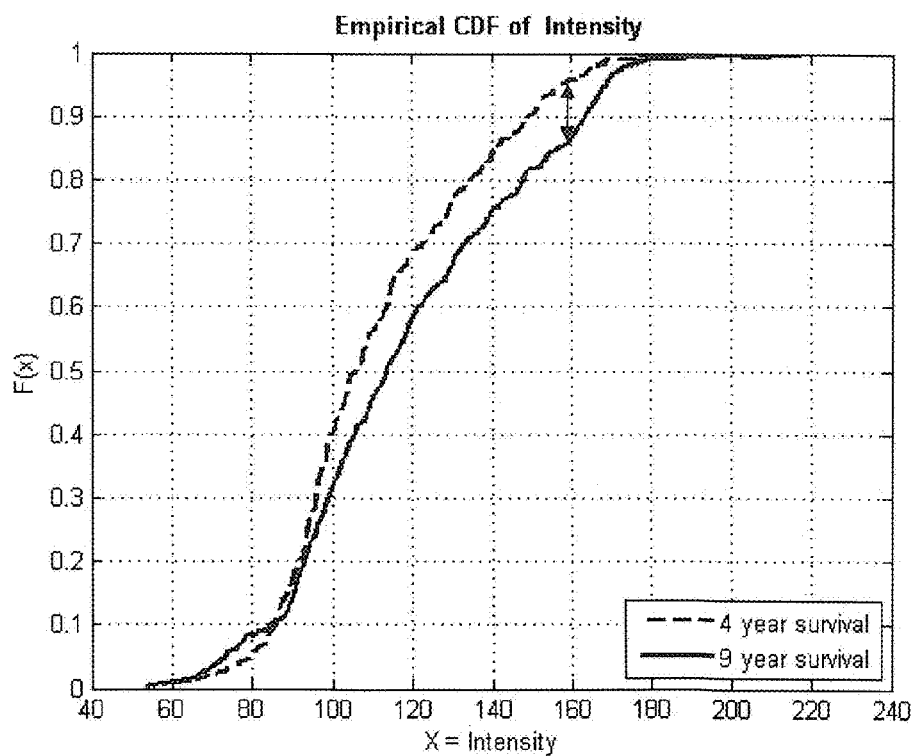
Figure 9E:
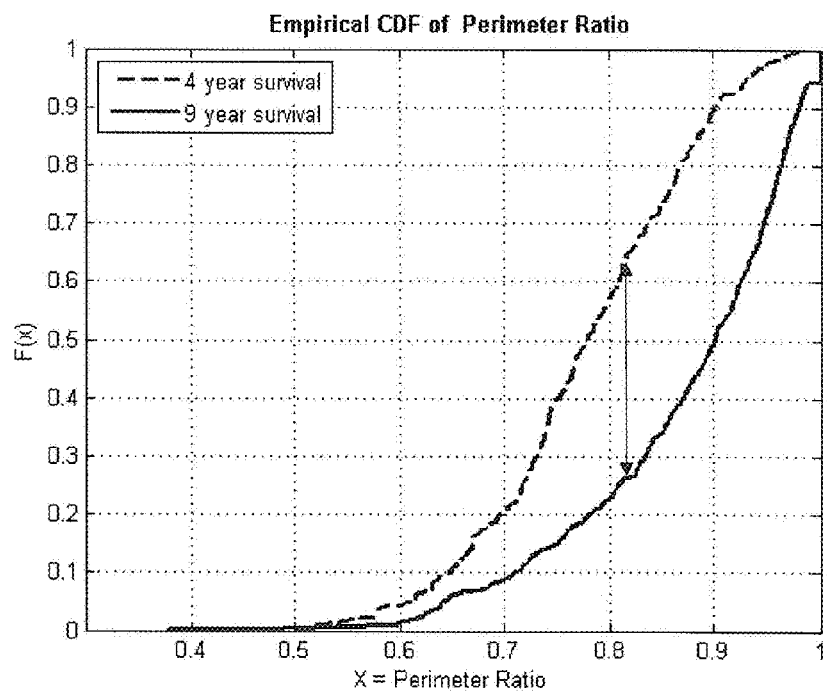
Figure 9F:
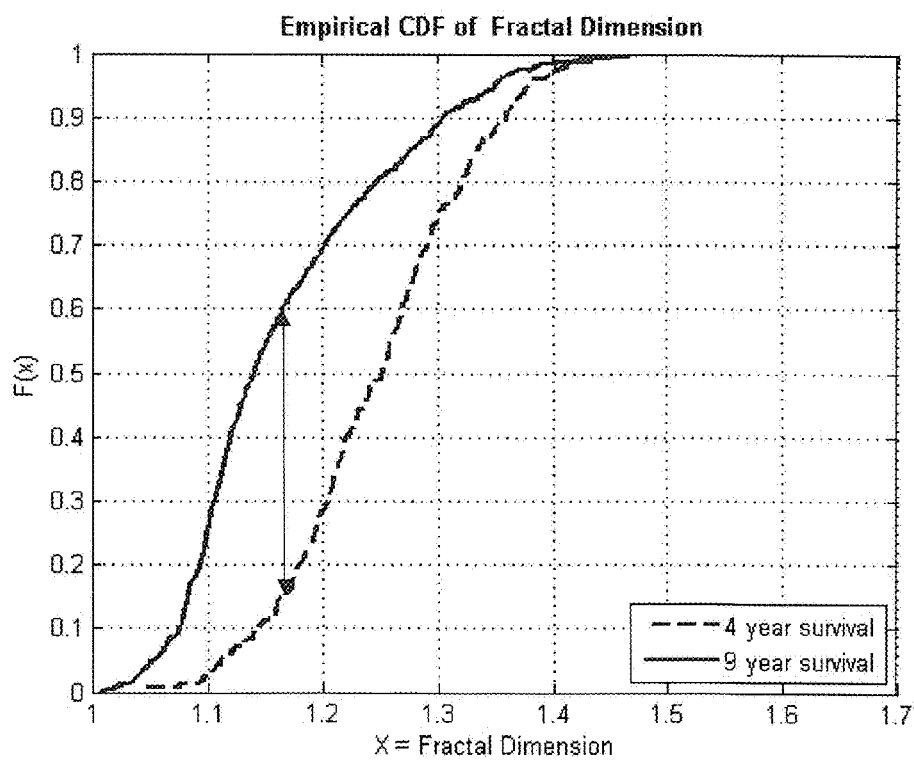
Figure 10A:
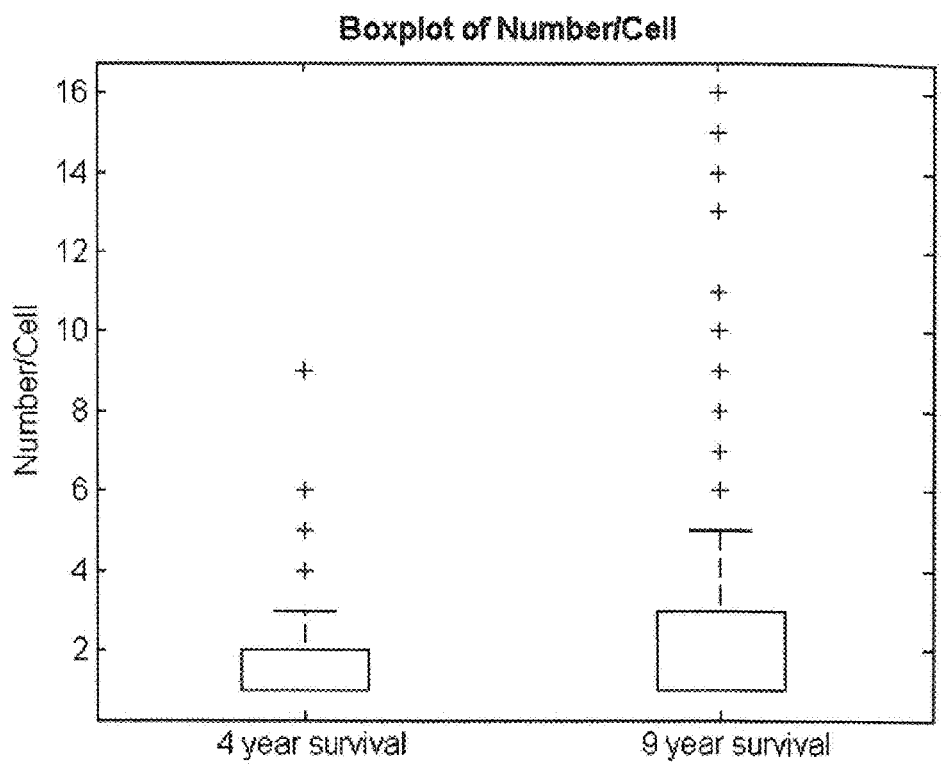
FIGS. 10A-10F show comparisons of median and distribution for 4-year (fatality) and 9-year (survivor) patients. For all six features, the six features have different medians and distributions.
Figure 10B:
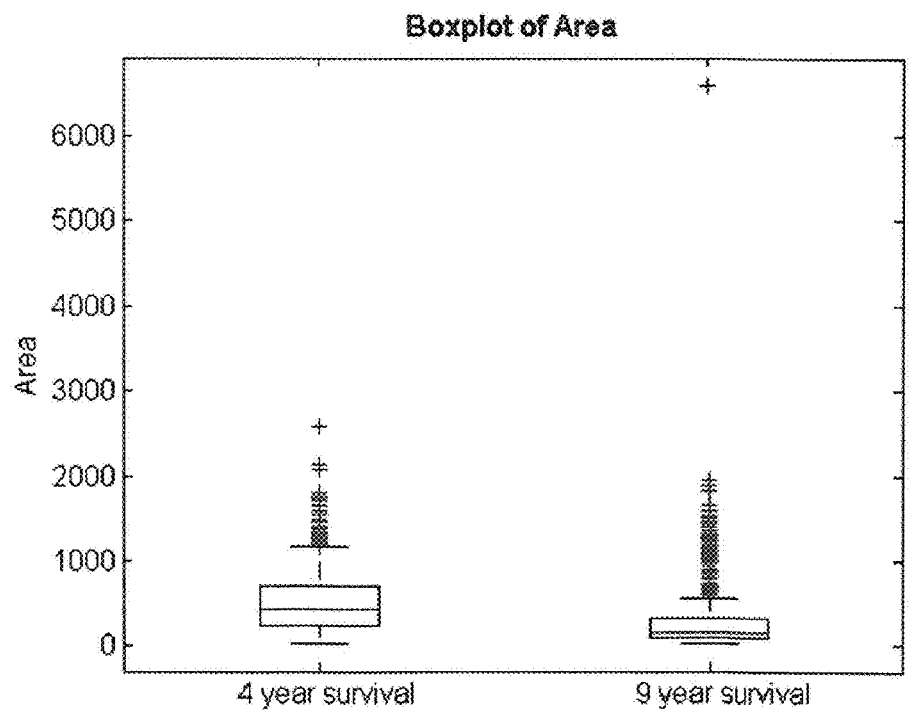
Figure 10C:
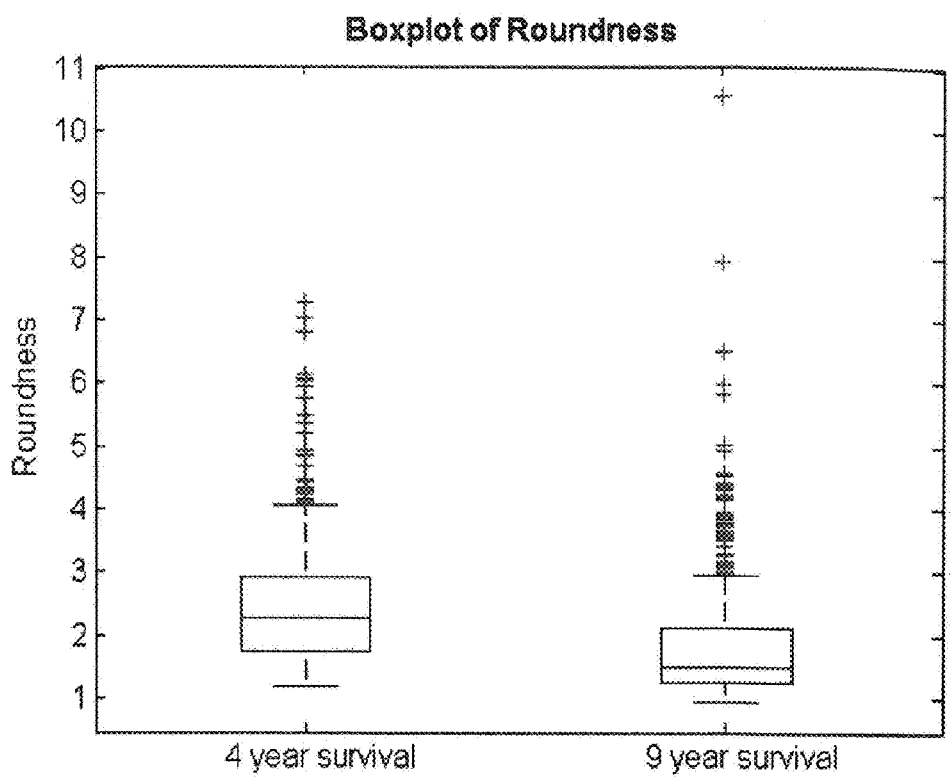
Figure 10D:
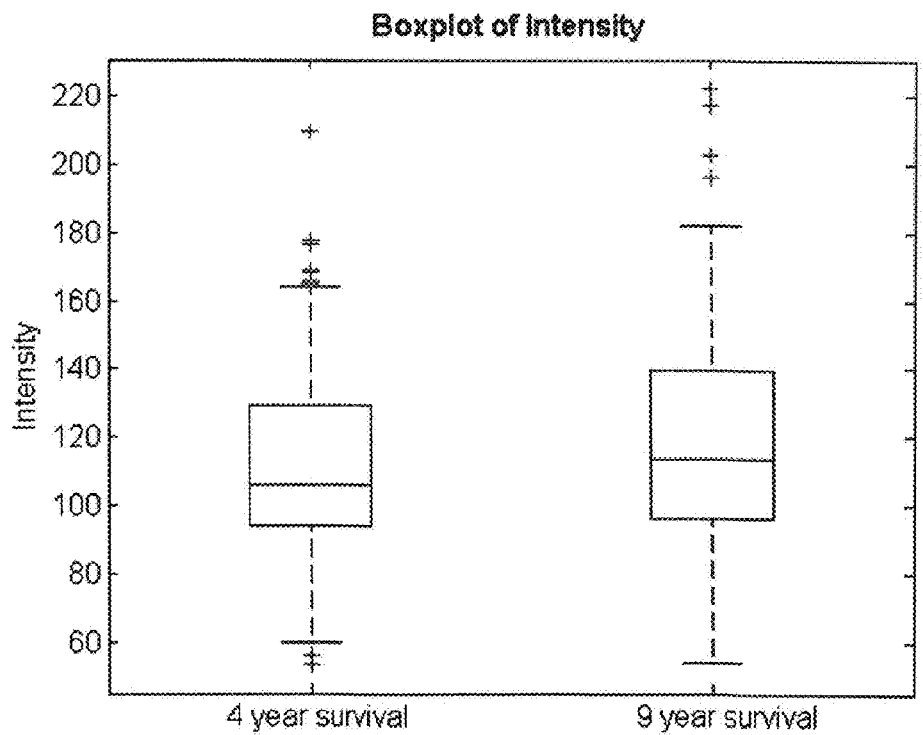
Figure 10E:
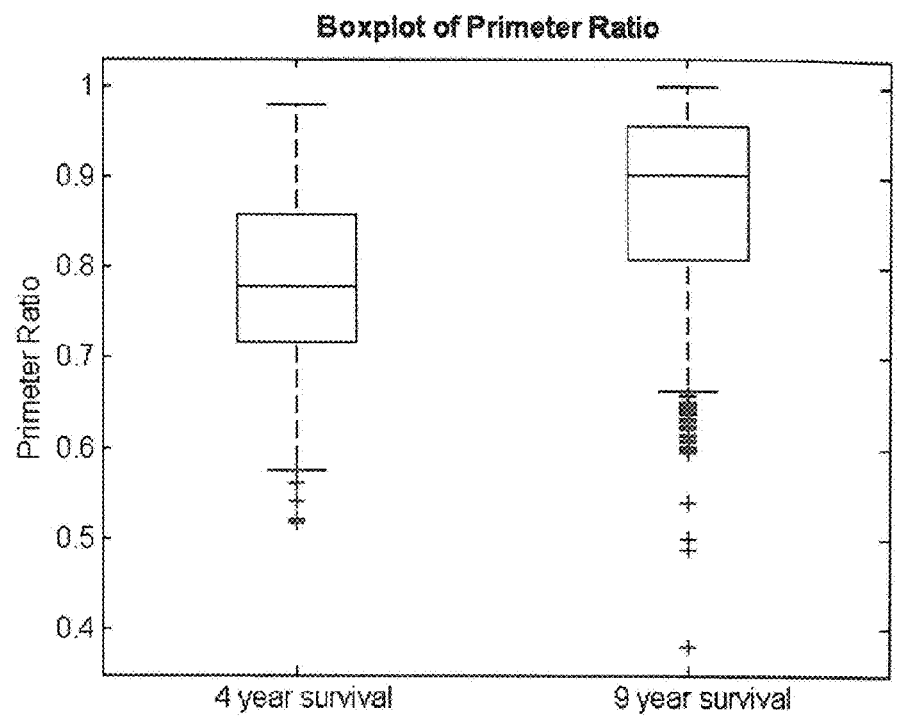
Figure 10F:
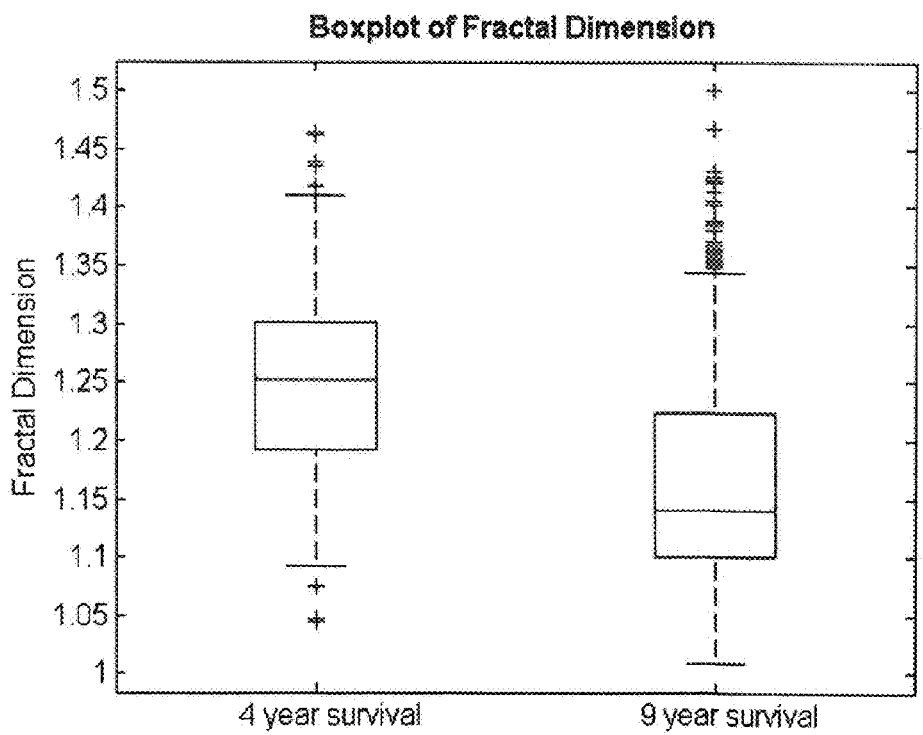

Then we test the performance of a classifier, linear discriminant analysis (LDA) with the feature number from one to 12 selected according to the optimized order. 10-fold cross-validation has been performed three times for every number of features. The results are shown in Table 5. We chose average of the three times test as test result. The distribution of error rate can be seen in FIG. 7. The error rate reached minimum when six features were selected (member/cell, area, roundness, intensity, perimeter ratio, fractal dimension). We used these six features as our feature set for statistical analysis, discriminant analysis, and classification.

TABLE 5

Error rate of 10-fold cross validation on linear discriminant analysis

| | Feature # | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| First test | 0.3677 | 0.3843 | 0.3167 | 0.3145 | 0.2746 | 0.2614 | 0.2636 | 0.2658 | 0.2713 | 0.2669 | 0.2636 | 0.268 |
| 2nd test | 0.3677 | 0.3798 | 0.3134 | 0.3123 | 0.2724 | 0.2602 | 0.2702 | 0.2647 | 0.2724 | 0.2691 | 0.2658 | 0.2702 |
| 3rd test | 0.3677 | 0.3754 | 0.3156 | 0.3134 | 0.2735 | 0.2636 | 0.2647 | 0.268 | 0.2658 | 0.268 | 0.2702 | 0.2724 |
| Average | 0.3677 | 0.3798 | 0.3152 | 0.3134 | 0.2735 | 0.2617 | 0.2662 | 0.2662 | 0.2698 | 0.2680 | 0.2665 | 0.2702 |

Statistical Analysis

1) Two-Sample t-Test

Two-sample tests can be used in either a descriptive or experimental design. In a descriptive design, two samples are randomly drawn from two different populations. If the analysis yields a significant difference, we conclude that the populations from which the samples were drawn are different. The test is carried out under the assumption that the two samples are independent and normally distributed with equal means under the null hypothesis (h=0) and different means under the alternative hypothesis (h=1). For small sample sizes, centrosome features may not be normally distributed; the central limit theorem guarantees that the sample mean is normally distributed, as long as the sample size is big enough (N≥30). Our sample sizes are N=309 and 594, respectively, which satisfies the requirement. Therefore, the two-sample t-test is applicable to our data (Terriberry (2005)).

2) Wilcoxon Rank Sum Test or Two-Sided Rank Sum Test

Wilcoxon rank-sum test is a non-parametric alternative to the two-sample t-test. Non-parametric statistics are not limited by parametric restrictions; it is sometimes called distribution-free method because it is not necessary to assume that the samples are normally distributed. Wilcoxon rank-sum test is much less sensitive to outliers than the two-sample t-test. These advantages make it more suitable for testing small samples with un-normal distribution and outliers. The null hypothesis of Wilcoxon rank sum test is that the two samples are independent from identical continuous distributions with equal medians, against the alternative that they do not have equal medians.

3) Kolmogorov-Smirnov (KS) Test

The Kolmogorov-Smirnov test is usually used to determine whether the two samples are drawn from the same distribution (the null hypothesis) or different distributions (the alternative hypothesis). The two-sample KS test is one of the most useful and general nonparametric methods for comparing two samples, as it is sensitive to differences in both location and shape of the empirical cumulative distribution functions of the two samples. The KS-test also has an advantage of making no assumption about the normal distribution of data.

Except h and p, the K-S test also returns the test statistic k, which quantifies the difference between distributions of the two samples and can be written as:

$$k = \text{Max}(|F_1(x) - F_2(x)|)$$

where $F_1(x)$ and $F_2(x)$ are empirical cumulative distribution functions of samples 1 and 2, respectively (Kozmann et al. (1991)).

Classification

1) Linear Discriminant Analysis

Linear discriminant analysis (LDA) is a well-known classification technique (Qiao et at (2009)). The approach of LDA is to project all the data points into new space of lower dimension, which maximizes the between-class variability and minimizes their within-class variability. For two categories of classification, the LDA finds an axis and projects all data points on this axis for distinguishing between the two classes. Allocation of a new point to a class can be accomplished by using a distance measurement. LDA is essentially a projection method.

2) Support Vector Machine

In general, Artificial Neural Network (ANN) or Support Vector Machine (SVM) outperforms LDA (Kumar and Bhattacharya (2006); Gokcen and Peng (2002)). A Support Vector Machine performs classification by transforming a nonlinear input data into higher dimensional space by using an appropriate kernel; then in the transformed space the data will be linearly separable. In SVM literature, a predictor variable is called an attribute, and a transformed attribute that is used to define the hyperplane is called a feature. A set of features that describes one case is called a vector. So, the goal of SVM modeling is to find the optimal hyperplane that separates clusters of vectors, cases with one category being on one side of the plane and cases with the other category being on the other side.

Results

1) Two-Sample t-Test Result

TABLE 6

Two-sample t-test test of 9 year survival vs. fatality after 4 years survival α = 0.05

| | Num/cell | Area | Roundness | Intensity | PerimRatio | FractalDimen |
|---|---|---|---|---|---|---|
| h | 1 | 1 | 1 | 1 | 1 | 1 |
| p | 3.04E−07 | 1.02E−13 | 5.32E−22 | 0.000747 | 2.22E−33 | 1.6858E−36 |
| ci | −1.465 | 168.788 | 0.554 | −10.631 | −0.107 | 0.070 |
| | −0.661 | 287.244 | 0.827 | −2.826 | −0.078 | 0.094 |

The test result for all six features h=1 indicates rejection of the null hypothesis, which means the two samples for all six features have different means and come from different populations. Returned p-values less than 0.001 for all six features indicate that the 99.9% confidence intervals (ci) on the mean differences of all six features do not contain zero, with 99.9% confidence that for all six features, there are significant mean differences between two populations. This result also suggests a feasibility to distinguish these two populations, which can be seen from FIGS. 8A-8F.

2) Wilcoxon Rank Sum Test or Two-Sided Rank Sum Test Result

TABLE 7

| Wilcoxon rank sum test of 9 years vs. 4 years survival α = 0.05 | | | | | |
|---|---|---|---|---|---|
| | Num/cell | Area | Roundness | Intensity | PerimRatio | FractalDimen |
| h | 1 | 1 | 1 | 1 | 1 | 1 |
| p | 7.01E−06 | 6.71E−27 | 6.45E−37 | 9.70E−04 | 1.57E−35 | 2.76E−37 |

The result rejects the null hypothesis for all six features with p-values less than 0.001, which indicates there are significant median differences between two different populations, with 99.9% confidence for all six features. The result is shown in the box plots in FIGS. 10A-10F.

3) Kolmogorov-Smirnov (KS) Test Result

TABLE 8

| Two-sample K-S test of 9 year vs. 4 year survival α = 0.05 | | | | | |
|---|---|---|---|---|---|
| | Num/cell | Area | Roundness | Intensity | PerimRatio | FractalDimen |
| h | 1 | 1 | 1 | 1 | 1 | 1 |
| p | 0.0015 | 5.87E−31 | 8.48E−34 | 4.20E−03 | 1.85E−30 | 1.87E−39 |
| k | 0.178 | 0.4122 | 0.4309 | 0.1221 | 0.4088 | 0.466 |

The two-sample Kolmogorov-Smirnov test is consistent with the two-sample t-test and Wilcoxon rank-sum test (see Tables 6, 7, and 8). The test verifies that all 6 centrosome features have different locations and shapes for four-year and nine-year survival patients (h=1). The largest p-value is 0.0015, which means that with 99.85% confidence, we can claim that distribution of every feature is different for two types of survival terms. The test also returns the values of statistic k that indicate whether the distances between cumulative distribution functions (CDFs) are sufficiently large enough to be considered distinct. Four features' k are bigger than 40% and the smallest value of k is 12.2%, which indicates that the distances between CDFs of the centrosome features for four-year and nine-year survival patients are large enough to distinguish them. The comparison is shown in FIGS. 9A-9F.

Three different statistical analysis methods have been carried out. These three methods quantitatively analyzed the data of the two samples from different aspects such as mean, median, location and shape. All the three methods have consistently proven that these two samples are from different populations. Therefore, they are distinguishable or can be classified. To verify how well they can be classified, we have applied two different classifiers on this data.

Classification

1) Result of Linear Discriminant Analysis

Training and Testing

The total of 903 centrosomes are split into training group and testing group. Even order numbers are selected for training and odd order numbers are selected for testing. The result is shown in Table 9.

TABLE 9

| Training and testing result of LDA | | | | | |
|---|---|---|---|---|---|
| Categories | Number | Error rate | Accurate rate | Sensitivity | Specificity |
| Training | 451 | 0.2683 | 0.7317 | 0.7987 | 0.6970 |
| Testing | 452 | 0.2655 | 0.7345 | 0.8323 | 0.6835 |
| Total | 903 | 0.2669 | 0.7331 | 0.8155 | 0.6902 |

Since the training data and testing data are selected (either manually or randomly), the training data may not represent the whole data. Results may vary if the classification is repeated with a different selection of training data and testing data. To avoid this variation and achieve overall performance evaluation, K-fold cross-validation has been performed (Kohavi (1995)). In K-fold cross-validation, the original sample is randomly partitioned into K subsamples. Of the K subsamples, a single subsample is retained as the validation data for testing the classifier, and the remaining K−1 subsamples are used as training data. The cross-validation process is then repeated K times (the folds), with each of the K subsamples used exactly once as the validation data. The K results from the folds then can be averaged to produce a single estimation. In this experiment, 10-fold cross-validation has been performed. The result is shown in Table 10:

TABLE 10

| 10-fold cross-validation result of LDA | | | | |
|---|---|---|---|---|
| | Error rate | Accurate rate | Sensitivity | Specificity |
| First test | 0.2614 | 0.7386 | 0.8026 | 0.7054 |
| Second test | 0.2602 | 0.7398 | 0.8155 | 0.7003 |
| Third test | 0.2636 | 0.7364 | 0.8058 | 0.7003 |
| Average | 0.2617 | 0.7383 | 0.8080 | 0.7020 |

The advantage of this method is that all observations are used for both training and validation, and each observation is used for validation exactly once. Therefore, the performance estimation represents an overall performance of a classifier on the whole data. Since the groups are selected randomly, there is small fluctuation for a different test. We tested three times and took the average as the result.

Compare table 9 and table 10, we can see these results are very close, which means the method we used for selection of training data and testing data is stable and reliable.

2) Classification Result of Support Vector Machine

For comparison, 10-fold cross-validation has been performed on SVM. The result is shown in Table 11. Compare Table 11 and Table 10; the accurate rate of SVM is somewhat better than LDA. The sensitivity of SVM is better than LDA. The specificity of LDA is better than SVM, which means LDA is more balanced on both categories than SVM for classification of this data.

TABLE 11

| | 10-fold cross-validation result of SVM (Linear kernel) | | | |
|---|---|---|---|---|
| | Error rate | Accurate rate | Sensitivity | Specificity |
| First test | 0.2140 | 0.7860 | 0.8395 | 0.6832 |
| Second test | 0.2143 | 0.7857 | 0.8394 | 0.6825 |
| Third test | 0.2138 | 0.7862 | 0.83395 | 0.6836 |
| Average | 0.2140 | 0.7860 | 0.8376 | 0.6831 |

Conclusion

The results show that individual long-term survival and fatality after short-term survival of stage I lung cancer patients can be distinguished by analysis and classification of centrosome features. Therefore, methods of the subject invention can be used to help doctors to design therapy for the individual patient.

Discussion

Since the classification object will not be individual centrosome, instead it will be individual patient case, which includes a group of centrosomes; thus, it is beneficial to classify a whole group of centrosomes into either a long-term survival category or a short-term survival category. Majority criterion will be applied in this case classification (Chiclana et al. (1995)). If a majority of centrosomes in a case is classified into the long-term survival category, the case will be classified into long-term survival category and vice versa. This criterion may increase sensitivity, specificity, and accuracy rate, since a patient case will be classified into the correct category if and only if more than 50% of the centrosomes of the patient analyzed will be classified into a correct category. After working with a well-selected classifier, any case will be able to be classified into one of the two categories in a high accuracy rate.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

References

Addison, Paul S. (1997) *Fractals and chaos an illustrated course*. Institute of Physics Publishing, ISBN 0 7503 0400 6 (pbk).

American Joint Committee on Cancer. (1998) *AJCC Cancer Staging Manual, 5th Edition*. Lippincott-Raven Pub. Philadelphia, Pa., ISBN 0-397-58419-9.

Barnsley, M. F. (1998) "Fractals everywhere" Academic Press.

Berrut, J-P. and Trefethen, L. N. (2004) "Barycentric Lagrange Interpolation" *SIAM Review*, 46(3):501-517.

Bourke E, Dodson H, Andreas Merdes A, Cuffe L, Zachos G, Walker M, Gillespie D, Morrison C G (2007) "DNA damage induces Chk1-dependent centrosome amplification" EMBO Rep., 8(6):603-609.

Brinkley, B. R. et al. (1998) "Supernumerary centrosomes and cancer: Boveri's hypothesis resurrected" *Cell Motil Cytoskeleton*, 41(4):281-8.

Chiclana, F., F. Herrera, E. Herrera-Viedma, M. C. Poyatos (1995) "A Classification Method of Alternatives for Multiple Preference Ordering Criteria Based on Fuzzy Majority" Technical Report #DECSAI-95115, E. T. S. de Ingenieria Informática, Universidad de Granada.

D'Amico, Thomas A. (2002) "Molecular biologic substaging of non-small cell lung cancer" *The Journal of Thoracic and Cardiovascular Surgery*, Editorials 409-410.

D'Amico, Thomas A., Thomas A. Aloia, Mary-Beth H. Moore, James E. Herndon I I, Kelli R. Brooks, Christine L. Lau, and David H. Harpole, Jr (2000) "Molecular Biologic Substaging of Stage I Lung Cancer According to Gender and Histology" *Ann Thorac Surg*, 69:882-6.

D'Assoro A B, Busby R, Acu I D, Quatraro C, Reinholz M M, Farrugia D J, Schroeder M A, Allen C, Stivala F, Galanis E, Salisbury J L (2008) "Impaired p53 function leads to centrosome amplification, acquired ERalpha phenotypic heterogeneity and distant metastases in breast cancer MCF-7 xenografts" Oncogene, 27(28):3901-11.

Ding, Chris and Peng, Hanchuan (2005) "Minimum redundancy feature selection from microarray gene expression data" *Journal of Bioinformatics and Computational Biology*, Vol. 3, No. 2, pp. 185-205.

Fukasawa, K. (2008) "p53, cyclin-dependent kinase and abnormal amplification of centrosomes" *Biochim Biophys Acta*, 1786(1):15-23.

Fukasawa, K. (2007) "Oncogenes and tumour suppressors take on centrosomes" *Nature Rev Cancer*, 7:911-924.

Gokcen, Ibrahim and Peng, Jing (2002) "Comparing Linear Discriminant Analysis and Support Vector Machines" A chapter from book, Advances in Information Systems. ISSN 0302-9743, pp 104-113.

Guo, Hui-qin, Meixia Gao, Jinfang Ma, Ting Xiao, Lin-lin Zhao, Yanning Gao and Qin-jing Pan (2007) "Analysis of the cellular centrosome in fine-needle aspirations of the breast" *Breast Cancer Research*, Vol 9 No 4.

Haralick, R. M., K. Shanmugan, and I. Dinstein (1973) "Textural Features for Image Classification" *IEEE Transactions on Systems, Man, and Cybernetics*, Vol. SMC-3, pp. 610-621.

Haralick, R. M. and Shapiro, L. G. (1992) "Computer and Robot Vision" Vol. 1, Addison-Wesley, p. 459.

Hontz A E, Li S A, Lingle W L, Negron V, Bruzek A, Salisbury J L, Li J J (2007) "Aurora a and B overexpression and centrosome amplification in early estrogen-induced tumor foci in the Syrian hamster kidney: implications for chromosomal instability, aneuploidy, and neoplasia" Cancer Res., 67(7):2957-63.

Hsu, L C, Kapali M, Deloia J A, Gallion H H (2005) "Centrosome abnormalities in ovarian cancer" *Int J Cancer*, 113:746-751. doi: 10.1002/ijc.20633.

Huck, J. J., Zhang, M., McDonald, A., Bowman, D., Hoar, K. M. et al. (2010) "MLN8054, an inhibitor of Aurora A kinase, induces senescence in human tumor cells both in vitro and in vivo" *Mol Cancer Res*, 8(3):373-384.

Jemal, A, Siegel, R, Ward, E, et al. (2009) "Cancer statistics, 2009" *CA Cancer J Clin*, 59:225.

Jung, C K, Jung J H, Lee K Y, Kang C S, Kim M, Ko Y H, Oh C S (2007) "Centrosome abnormalities in non-small cell lung cancer: Correlations with DNA aneuploidy and expression of cell cycle regulatory proteins" *Pathology Research and Practice*, 203(12):839-847.

Kawamura, K, Moriyama M, Shiba N, Ozaki M, Tanaka T, Nojima T, Fujikawa-Yamamoto K, Ikeda R, Suzuki K (2003) "Centrosome hyperamplification and chromosomal instability in bladder cancer" *Eur Urol.*, 43:505-515. doi: 10.1016/S0302-2838(03)00056-3.

Kohavi, Ron (1995) "A study of cross-validation and bootstrap for accuracy estimation and model selection" *Proceedings of the Fourteenth International Joint Conference on Artificial Intelligence*, 2(12):1137-1143 (Morgan Kaufmann, San Mateo).

Koutsami, M K, Tsantoulis P K, Kouloukoussa M, Apostolopoulou K, Pateras I S, Spartinou Z, Drougou A, Evangelou K, Kittas C, Bartkova J, Bartek J, Gorgoulis V G (2006) "Centrosome abnormalities are frequently observed in non-small-cell lung cancer and are associated with aneuploidy and cyclin E overexpression" *Journal of pathology*, 209(4):512-521.

Kozmann, Gyorgy, Larry S. Green, and Robert L. Lux (1991) "Nonparametric Identification of Discriminative Information in Body Surface Maps" *IEEE Transactions on Biomedical Engineering*, Vol. 3R. No II. 1061-1068.

Kumar, Kuldeep and Bhattacharya, Sukanto (2006) "Artificial neural network vs linear discriminant analysis in credit ratings forecast" *Review of Accounting and Finance*, Vol. 5 No. 3, pp. 216-227.

Kwiatkowski, David J., David H. Harpole, Jr, John Godleski, James E. Herndon I I, Dar-Bin Shieh, William Richards, Ramon Blanco, Hong-Ji Xu, Gary M. Strauss, and David J. Sugarbaker (1998) "Molecular Pathologic Substaging in 244 Stage I Non-Small-Cell Lung Cancer Patients: Clinical Implications" *Journal of Clinical Oncology*, Vol 16, No 7 (July), pp 2468-2477.

Landen, Jr., Charles N., Yvonne G. Lin, Anand Immaneni, Michael T. Deavers, WilliamM. Merritt, Whitney A. Spannuth, Diane C. Bodurka, DavidM. Gershenson, William R. Brinkley, and Anil K. Sood (2007) "Overexpression of the Centrosomal Protein Aurora-A Kinase is Associated with Poor Prognosis in Epithelial Ovarian Cancer Patients" *Clin Cancer Res*, 13(14).

Lentini, Laura, Angela Amato, Tiziana Schillaci, and Aldo Di Leonardo (2007) "Simultaneous Aurora-A/STK15 overexpression and centrosome amplification induce chromosomal instability in tumor cells with a MIN phenotype" *Clin Cancer Res*, 13(14):4098-4104.

Manfredi, M. G., Ecsedy, J. A., Meetze, K. A., Balani, S. K., Burenkova, O. et al. (2007) "Antitumor activity of MLN8054, an orally active small-molecule inhibitor of Aurora A kinase" *PNAS*, 104(10):4106-4111.

Michalak, Krzysztof and Halina Kwa'Snicka (2006) "Correlation-based feature selection strategy in classification problems" *Int. J. Appl. Math. Comput. Sci.*, 16(4):503-511.

Nigg, E. A. (2002) "Centrosome aberrations: cause or consequence of cancer progression?" *Nature Rev Cancer*, 2:815-825.

Peng, Hanchuan, Fuhui Long, and Chris Ding (2005) "Feature selection based on mutual information: criteria of max-dependency, max-relevance, and min-redundancy" *IEEE Transactions on Pattern Analysis and Machine Intelligence*, Vol. 27, No. 8, pp. 1226-1238.

Piel M, Nordberg J, Euteneuer U, Bornens M. (2001) "Centrosome-dependent exit of cytokinesis in animal cells" *Science*, 291(5508):1550-3.

Pihan, G A, Purohit A, Wallace J, Malhotra R, Liotta L, Doxsey S J (2001) "Centrosome defects can account for cellular and genetic changes that characterize prostate cancer progression" *Cancer Res.*, 61:2212-2219.

Qiao, Zhihua, Lan Zhou and Jianhua Huang (2009) "Sparse Linear Discriminant Analysis with application to high dimension low sample size data" *IAENG Int. J. Appl. Math.*, vol. 39, no. 1, 48-60.

Rami-Porta, Ramon, John J. Crowley, Peter Goldstraw (2009) "The Revised TNM Staging System for Lung Cancer" *Ann Thorac Cardiovasc Surg*, Vol. 15, No. 1.

Salisbury J L, D'Assoro A B, Lingle W L (2004) "Centrosome amplification and the origin of chromosomal instability in breast cancer" *J Mammary Gland Biol Neoplasia.*, 9(3):275-83. Review.

Saunders, William (2005) "Review: Centrosomal amplification and spindle multipolarity in cancer cells", *Seminars in Cancer Biology*, 15:25-32.

Shinmura, K, M Lwaizumi, H Lgarashi, K Nagura, H Yamada, M Suzuki, K Fukasawa, and H Sugimura (2008) "Induction of centrosome amplification and chromosome instability in p53-deficient lung cancer cells exposed to benzo[α]pyrene diol epoxide" *Journal of Pathology*, 216: 365-374.

Shono, M, Sato N, Mizumoto K, Maehara N, Nakamura M, Nagai E, Tanaka M. (2001) "Stepwise progression of centrosome defects associated with local tumor growth and metastatic process of human pancreatic carcinoma cells transplanted orthotopically into nude mice" *Lab Invest.*, 81:945-952.

Terriberry, Timothy B., Sarang C. Joshi, and Guido Gerig (2005) "Hypothesis Testing with Nonlinear Shape Models" *Information Processing in Medical Imaging, LNCS*3565, 15-26.

Woo T, Okudela K, Yazawa T, et al. (2009) "Prognostic value of KRAS mutations and Ki-67 expression in stage I lung adenocarcinomas" *Lung Cancer*, 65(3):355-62.

Wunderlich, V. (2002) "JMM—past and present chromosomes and cancer: Theodor Boveri's predictions 100 years and later" *Jol Mol Med*, 80(9):545-48.

Yin, P -Y. (2002) "Maximum entropy-based optimal threshold selection using deterministic reinforcement learning with controlled randomization" *Signal Processing*, 82:993-1006.

Zuiderveld, Karel (1994) "Contrast Limited Adaptive Histograph Equalization" *Graphic Gems IV*. San Diego: Academic Press Professional, pp. 474-485.

We claim:

1. A method for providing a prognosis of cancer for a person or animal prior to treatment of the cancer, the method comprising:

obtaining an image of one or more cells;

selecting a region of interest that comprises one or more cells, wherein the cell comprises at least one centrosome;

segmenting the selected region of interest for the cell, wherein the at least one centrosome of the cell is delineated from other parts of the cell;

extracting at least one feature from each of the at least one delineated centrosome of the cell;

analyzing the extracted feature from each of the at least one delineated centrosome of the cell; and providing a prognosis of cancer based on one or more results of the analysis prior to treatment of the cancer.

2. The method of claim 1, wherein one or more of the at least one extracted feature is centrosome number per cell, centrosome area, fragment, intensity, intensity standard deviation, area to box ratio, aspect, mean diameter, perimeter ratio, roundness, fractal dimension, solidity, or eccentricity.

3. The method of claim 1, wherein the analysis comprises a statistical analysis.

4. The method of claim 1, wherein the image is acquired via a tandem-scanning confocal microscope.

5. The method of claim 1, the method further comprising enhancing the image of the one or more cells.

6. The method of claim 1, the method further comprising classifying the results of the analysis to determine a prognosis of cancer survival for the person or animal.

7. The method of claim 6, wherein the prognosis is for long-term cancer survival or for short-term cancer survival.

8. The method of claim 6, wherein increased centrosomal number/cell; decreased area; decreased roundness; increased intensity; increased perimeter ratio; and/or decreased fractal dimension is associated with a prognosis of long-term cancer survival.

9. The method of claim 1, wherein at least six centrosomal features are extracted and analyzed.

10. The method of claim 9, wherein the at least six centrosomal features comprise number/cell, area, roundness, intensity, perimeter ratio, and fractal dimension.

11. The method of claim 1, wherein at least five centrosomal features are extracted and analyzed.

12. The method of claim 11, wherein the at least five centrosomal features comprise number/cell, area, intensity, fragment, and aspect.

13. The method of claim 1, wherein one or more of the steps of the method are performed by one or more suitably programmed computers.

14. The method of claim 13, wherein computer executable instructions for performing one or more of the steps of the method are provided on one or more computer readable media.

15. The method of claim 1, wherein the method is performed using an image processing system.

16. One or more non-transitory computer-readable media having computer-useable instructions embodied thereon for performing a method for diagnosing cancer and/or providing a prognosis for a person or animal, the method comprising:
  receiving an image of one or more cells;
  selecting a region of interest that comprises one cell, wherein the cell comprises at least one centrosome;
  segmenting the selected region of interest for the cell, wherein each at least one centrosome of the cell is delineated from other parts of the cell;
  extracting at least one feature from each of the at least one delineated centrosome of the cell;
  analyzing the at least one extracted feature from each of the at least one delineated centrosome of the cell; and
  diagnosing cancer and/or providing a prognosis based on one or more results of the analysis, wherein the non-transitory media is selected from the group consisting of information-delivery media, RAM, ROM, EEPROM, flash memory, CD-ROM, digital versatile disc (DVD), holographic media or other optical disc storage, magnetic cassette, magnetic tape, magnetic disk storage, and other magnetic storage devices.

17. The non-transitory media of claim 16, wherein at least six centrosomal features are extracted and analyzed.

18. The non-transitory media of claim 17, wherein the at least six centrosomal features comprise number/cell, area, roundness, intensity, perimeter ratio, and fractal dimension.

19. The non-transitory media of claim 16, wherein at least five centrosomal features are extracted and analyzed.

20. One or more non-transitory computer-readable media having computer-useable instructions embodied thereon for performing a method for providing a prognosis of cancer for a person or animal prior to treatment of the cancer, the method comprising:
  receiving an image of one or more cells;
  selecting a region of interest that comprises one cell, wherein the cell comprises at least one centrosome;
  segmenting the selected region of interest for the cell, wherein each at least one centrosome of the cell is delineated from other parts of the cell;
  extracting at least one feature from each of the at least one delineated centrosome of the cell;
  analyzing the at least one extracted feature from each of the at least one delineated centrosome of the cell; and
  providing a prognosis of cancer based on one or more results of the analysis prior to treatment of the cancer.

* * * * *